(12) United States Patent
Liu et al.

(10) Patent No.: US 10,950,353 B2
(45) Date of Patent: Mar. 16, 2021

(54) SYSTEMS AND METHODS FOR DISEASE PROGRESSION MODELING

(71) Applicants: GEORGIA TECH RESEARCH CORPORATION, Atlanta, GA (US); UNIVERSITY OF PITTSBURGH-OF THE COMMONWEALTH SYSTEM OF HIGHER EDUCATION, Pittsburgh, PA (US)

(72) Inventors: Yu-Ying Liu, Santa Clara, CA (US); Hiroshi Ishikawa, Wexford, PA (US); James Rehg, Atlanta, GA (US); Joel S. Schuman, Pittsburgh, PA (US); Gadi Wollstein, Pittsburgh, PA (US)

(73) Assignees: Georgia Tech Research Corporation, Atlanta, GA (US); University of Pittsburgh-of the Commonwealth System of Higher Education, Pittsburgh, PA (US)

( * ) Notice: Subject to any disclaimer, the term of this patent is extended or adjusted under 35 U.S.C. 154(b) by 1078 days.

(21) Appl. No.: 15/022,711

(22) PCT Filed: Sep. 19, 2014

(86) PCT No.: PCT/US2014/056671
§ 371 (c)(1),
(2) Date: Mar. 17, 2016

(87) PCT Pub. No.: WO2015/042476
PCT Pub. Date: Mar. 26, 2015

(65) Prior Publication Data
US 2016/0232324 A1    Aug. 11, 2016

Related U.S. Application Data

(60) Provisional application No. 61/880,246, filed on Sep. 20, 2013.

(51) Int. Cl.
*G16H 50/50* (2018.01)
*G16H 10/60* (2018.01)
(Continued)

(52) U.S. Cl.
CPC ............ *G16H 50/50* (2018.01); *A61B 5/4842* (2013.01); *G06N 5/022* (2013.01); *G16H 10/60* (2018.01); *G16H 50/20* (2018.01); *A61B 5/7275* (2013.01)

(58) Field of Classification Search
CPC ........ G16H 50/50; G16H 10/60; G16H 50/20; G06N 5/022; A61B 5/4842
See application file for complete search history.

(56) References Cited

U.S. PATENT DOCUMENTS 7,480,640 B1    1/2009  Elad et al.
8,249,731 B2    8/2012  Tran et al.
(Continued)

OTHER PUBLICATIONS

Yuanxi Li et al., "Modelling and analysing the dynamics of disease progression from cross-sectional studies", Nov. 2012, Journal of Biomedical Informatics, 46 (2013) 266-274 (Year: 2012).*

(Continued)

*Primary Examiner* — Evangeline Barr
(74) *Attorney, Agent, or Firm* — Troutman Pepper Hamilton Sanders LLP; Ryan A. Schneider; Dustin B. Weeks

(57) ABSTRACT

A method for determining a disease state transition path includes receiving a patient data having functional data and/or structural data related to a patient. Based on the patient data, a first disease state of a plurality of non-overlapping disease states each associated with a predetermined range of functional and/or structural degeneration values may be identified. A second, non-adjacent disease state of the plurality of disease states may be identified based on the patient data. A most probable path between the first (Continued)

disease state and the second disease state may be determined using a two dimensional continuous-time hidden Markov model.

14 Claims, 16 Drawing Sheets

(51) Int. Cl.
  *G16H 50/20* (2018.01)
  *A61B 5/00* (2006.01)
  *G06N 5/02* (2006.01)

(56) References Cited

U.S. PATENT DOCUMENTS

| | | | |
|---|---|---|---|
| 8,388,530 | B2 | 3/2013 | Shusterman |
| 2008/0004904 | A1 | 1/2008 | Tran |
| 2009/0054740 | A1 | 2/2009 | Gudmundsson et al. |
| 2011/0028827 | A1 | 2/2011 | Sitaram et al. |
| 2011/0112380 | A1 | 5/2011 | Robinson |
| 2011/0190657 | A1 | 8/2011 | Zhou et al. |
| 2012/0287401 | A1 | 11/2012 | Bizios et al. |
| 2013/0108598 | A1 | 5/2013 | Oresic et al. |
| 2013/0116999 | A1* | 5/2013 | Stein .................... G16H 50/50 703/11 |

OTHER PUBLICATIONS

Jackson et al., "Multistate Markov models for disease progression with classification error", 2003, Royal Statistical Society, The Statistician, 52, Part 2, pp. 193-209 (Year: 2003).*
Christopher Jackson, et al., "Multistate Markov models for disease progression with classification error", 2003, The Statistician, 52, Part 2, pp. 193-209 (Year: 2003).*
Altman, R.M. et al., "Application of hidden Markov models to multiple sclerosis lesion count data," Statist. Med., 2005, pp. 2335-2344, 24(15), John Wiley & Sons, Ltd.
Bartolomeo, N. et al., "Progression of liver cirrhosis to HCC: an application of hidden Markov model," BMC Medical Research Methodology, 2011, Research Article, 11:38.
Bicego, M. et al., "Investigating Hidden Markov Models' Capabilities in 2D Shape Classification," IEEE Trans. Pattern Anal. Mach. Intell., 2004, pp. 281-286, 26(2), IEEE.
Bowd, C. et al., "Bayesian Machine Learning Classifiers for Combining Structural and Functional Measurements to Classify Healthy and Glaucomatous Eyes," Invest. Ophth. Vis. Sci., 2008, pp. 945-953, 49(3).
Bryan, S.R. et al., "Robust and Censored Modeling and Prediction of Progression in Glaucomatous Visual Fields," Invest. Ophth. Vis. Sci., 2013, pp. 6694-6700, 54(10).
Bureau, A. et al., "Applications of continuous time hidden Markov models to the study of misclassified disease outcomes," Stat. Med., 2003, pp. 441-462, 22(3), John Wiley & Sons, Ltd.
Burgansky-Eliash, Z. et al., "Optical Coherence Tomography Machine Learning Classifiers for Glaucoma Detection: A Preliminary Study," Invest. Ophth. Vis. Sci., 2005, pp. 4147-4152; 46(11).
Cai, J. et al., "Hidden Markov Models with Spectral Features for 2D Shape Recognition," IEEE Trans. Pattern Anal. Mach. Intell., 2001, pp. 1454-1458, 23(12), IEEE.

Congdon, N. et al., "Causes and Prevalence of Visual Impairment Among Adults in the United States," Arch. Ophthalmol., 2004, pp. 477-485, 122(4).
Cooper, B., "The analysis of hospital infection data using hidden Markov models," Biostatistics, 2004, pp. 223-237, 5(2), Oxford University Press.
El-Manzalawy, Y. et al., "Predicting Flexible Length Linear B-Cell Epitopes," Comput. Syst. Bioinformatics Conf., 2008, pp. 121-132, 7.
Fonteijn, H.M. et al., "An event-based model for disease progression and its application in familial Alzheimers disease and Huntingtons disease," Neuroimage, 2012, pp. 1880-1889, 60(3), Elsevier Inc.
Grewal, D.S. et al., "Detection of Progressive Retinal Nerve Fiber Layer Thickness Loss with Optical Coherence Tomography Using Three Criteria for Functional Progression," J. Glaucoma, 2012, pp. 214-220, 21(4).
Harwerth, R.S. et al., "Linking Structure and Function in Glaucoma," Prog. Retin. Eye Res., 2010, pp. 249-271, 29(4).
Hassan, R. et al., "A Data Clustering Algorithm Based on Single Hidden Markov Model," Proceedings of the International Multiconference on Computer Science and Information Technology, 2006, pp. 57-66.
Jackson, C.H, "Multi-State Models for Panel Data: The msm Package for R," J. Stat. Softw, 2011, 28 pgs, 38(8).
Juang, B-H. et al., "The Segmental K-Means Algorithm for Estimating Parameters of Hidden Markov Models," IEEE Trans. Acoust., Speech, Signal Processing, 1990, pp. 1639-1641, 38(9), IEEE.
Kalbfleisch, J.D. et al., "The Analysis of Panel Data Under a Markov Assumption," J. Amer. Statist. Assoc., 1985, pp. 863-871, 80(392), Taylor & Francis, Ltd.
Kingman, S., "Glaucoma is second leading cause of blindness globally," Bull. World Health Organ., 2004, pp. 887-888, 82(11).
Kotowski, J. et al., "Clinical Use of OCT in Assessing Glaucoma Progression," Ophthalmic Surg Lasers Imaging, 2011, pp. S6-S14, 42(0).
Lee, A.Y. et al., "Circadian Rhythm Patterns in Patients with Advanced Glaucoma," Invest. Ophth. Vis. Sci., 2011, Abstract, 52(14).
Leiva-Murillo, J.M. et al., "Visualization and Prediction of Disease Interactions with Continuous-Time Hidden Markov Models," Neural Information Processing Systems (NIPS) 2011 Workshop on Personalized Medicine, 2011.
Leung, C.K. et al., "Evaluation of Retinal Nerve Fiber Layer Progression in Glaucoma: A Prospective Analysis with Neuroretinal Rim and Visual Field Progression," Ophthalmology, 2011, pp. 1551-1557, 118(8).
Quigley, H.A. et al., "Models of Open-Angle Glaucoma Prevalence and Incidence in the United States," Invest. Ophth. Vis. Sci., 1997, pp. 83-91, 38(1).
Racette, L. et al., "Combining Functional and Structural Tests Improves the Diagnostic Accuracy of Relevance Vector Machine Classifiers," J. Glaucoma, 2010, pp. 167-175. 19(3).
Rabiner, L.R., "A Tutorial on Hidden Markov Models and Selected Applications in Speech Recognition," Proc. of the IEEE, 1989, pp. 257-286, 77(2), IEEE.
Titman, A.G., "Model diagnostics in multi-state models of biological systems," Dissertation-Fitzwilliam College, University of Cambridge, 2007.
Wang, Y. et al., "Spatio-temporal Analysis of Brain MRI Images Using Hidden Markov Models," Med Image Comput Comput Assist Interv, 2010, pp. 160-168, 13(02).
International Search Report for related Application No. PCT/US2014/056671 dated Jan. 14, 2015.

* cited by examiner

SYSTEMS AND METHODS FOR DISEASE PROGRESSION MODELING

CROSS-REFERENCE TO RELATED APPLICATIONS AND PRIORITY CLAIM

This application is a national stage application based on PCT/US2014/056671, with an international filing date of 19 Sep. 2014, which claims priority to U.S. Provisional Patent Application No. 61/880,246, filed 20 Sep. 2013 and entitled "Disease Progression Modeling in Structural and Functional Dimensions using 2-D Continuous-time Hidden Markov Model," the contents of each of which are fully incorporated herein by reference.

STATEMENT REGARDING FEDERALLY SPONSORED RESEARCH

This invention was made with government support under Grant No. 5R01EY013178-13, awarded by DHHS/PHS/National Institutes of Health (NIH) and under IIS-0916687, awarded by National Science Foundation. The government has certain rights in the invention.

FIELD OF THE INVENTION

The invention relates generally to systems and methods for disease progression modeling and more specifically to systems and methods for disease progression modeling in two dimensions, and in one example they can be structural and functional dimensions.

BACKGROUND

Glaucoma is an optic neuropathy characterized by progressive loss of retinal ganglion cells and damage of the optic nerve. Called the "silent thief of sight," glaucoma causes a loss of vision that often occurs gradually without the patient's awareness until the disease has advanced significantly. If left untreated, glaucoma may cause irreversible visual field deficits and even blindness. Due to its irreversible effects, early identification of glaucoma and its progression, and delivery of appropriate treatment are critical to retard the deterioration and preserve sight.

Several clinical techniques for structural and functional measurement are often utilized for glaucoma monitoring. For example, 3D optical tomography is used to examine the optic nerve head, and psychophysical techniques, such as automated perimetry, are applied to assess the status of the visual field. Even with these measurement techniques, identification of glaucoma progression is often challenging for at least three reasons. First, glaucoma is a slowly progressing disease, and it is difficult to discriminate between true disease-related changes and natural age-related degeneration. Second, the rate of functional and structural progression among patients can be highly variable, and thus, it is hard to establish one rule of thumb for progression detection. Third, structural and functional changes often occur at different times over the disease course (e.g., a patient experiencing substantial structural loss before any evidence of visual field deficits emerges). Due to these difficulties, there is no widely accepted standard for establishing glaucoma progression considering both types of damages.

Current approaches for monitoring glaucoma disease progression include subjective assessment and statistical analysis of measurements collected over time. The statistical approaches can be divided into event-based and trend-based methods. In event analysis, progression is identified when a follow-up measurement exceeds a pre-established threshold of change from a baseline measurement. In trend analysis, the behavior of a parameter is monitored over time using methods such as linear regression. Generally, the event-based or trend-based analysis is applied separately to each measurement.

While the event-based and trend-based statistical analyses can be helpful in monitoring glaucoma disease progression, they fail to consider all types of measurements to determine the true disease course for glaucoma progression assessment. As a result, event-based and trend-based statistical analyses may not accurately capture an underlying disease stage, identify fast progression between certain disease states, determine progression of the disease between measurements, and predict future disease states based on known disease progression data. Embodiments of the present invention address this need as well as other needs that will become apparent upon reading the description below in conjunction with the drawings.

SUMMARY

Examples of the disclosed technology include a method for determining a disease state transition path. In one example implementation, a method is provided that may include receiving patient data having one or both of functional data and structural data related to a patient. Based on the patient data, a first disease state of a plurality of non-overlapping disease states each associated with a predetermined range of one or both of functional and structural degeneration values may be identified. Further, a second disease state of the plurality of disease states may be identified based on the second set of patient data. The second disease state may be non-adjacent to the first disease state. After identifying the non-adjacent first and second disease states, a most probable path between the first disease state and the second disease state may be determined using a two dimensional continuous-time hidden Markov model. The most probable path may have one or more intermediary disease states of the plurality of disease states. Each intermediary disease state may be adjacent to one or more of the first disease state, the second disease state, and another intermediary disease state.

A method for detecting disease state transitions having fast progression is also disclosed, according to an example implementation of the disclosed technology. The method may include receiving patient data having one or both of functional data and structural data related to a patient. Based on the patient data, a first disease state of a plurality of non-overlapping disease states each associated with a predetermined range of one or both of functional and structural degeneration values may be identified. Further, a second disease state of the plurality of disease states may be identified based on the patient data. The second disease state may be non-adjacent to the first disease state. The method may further include determining, using a hidden Markov model, a most probable path between the first disease state and the second disease state. The most probable path may have one or more intermediary disease states of the plurality of disease states. Each intermediary disease state may be adjacent to one or more of the first disease state, the second disease state, and another intermediary disease state. A most probable next state for one or more disease states along the most probable path may be determined using the hidden Markov model. Additionally, the most probable next disease state may be compared with the second disease state. Further, a transition between disease states along the most probable path may be determined as having a fast structural and/or functional progression based on the comparison.

A system for determining a disease state transition path is provided, according to an example implementation of the disclosed technology. The system may include a storage device for storing instructions, and a processor configured to execute the instructions in the storage device to receive patient data having one or both of functional data and structural data related to a patient. The processor may also be configured to identify, based on the patient data, a first disease state of a plurality of non-overlapping disease states each associated with a predetermined range of one or both of functional and structural degeneration values. A second disease state of the plurality of disease states may be identified by the processor based on the patient data. The second disease state may be non-adjacent to the first disease state. The processor may further be configured to determine, using a two dimensional continuous-time hidden Markov model, a most probable path between the first disease state and the second disease state. The most probable path may have one or more intermediary disease states of the plurality of disease states. Each intermediary disease state may be adjacent to one or more of the first disease state, the second disease state, and another intermediary disease state.

BRIEF DESCRIPTION OF THE DRAWINGS

The drawing figures depict one or more implementations in accord with the present teachings, by way of example only, not by way of limitation. In the figures, like reference numerals refer to the same or similar elements.

DETAILED DESCRIPTION

Figure 1:
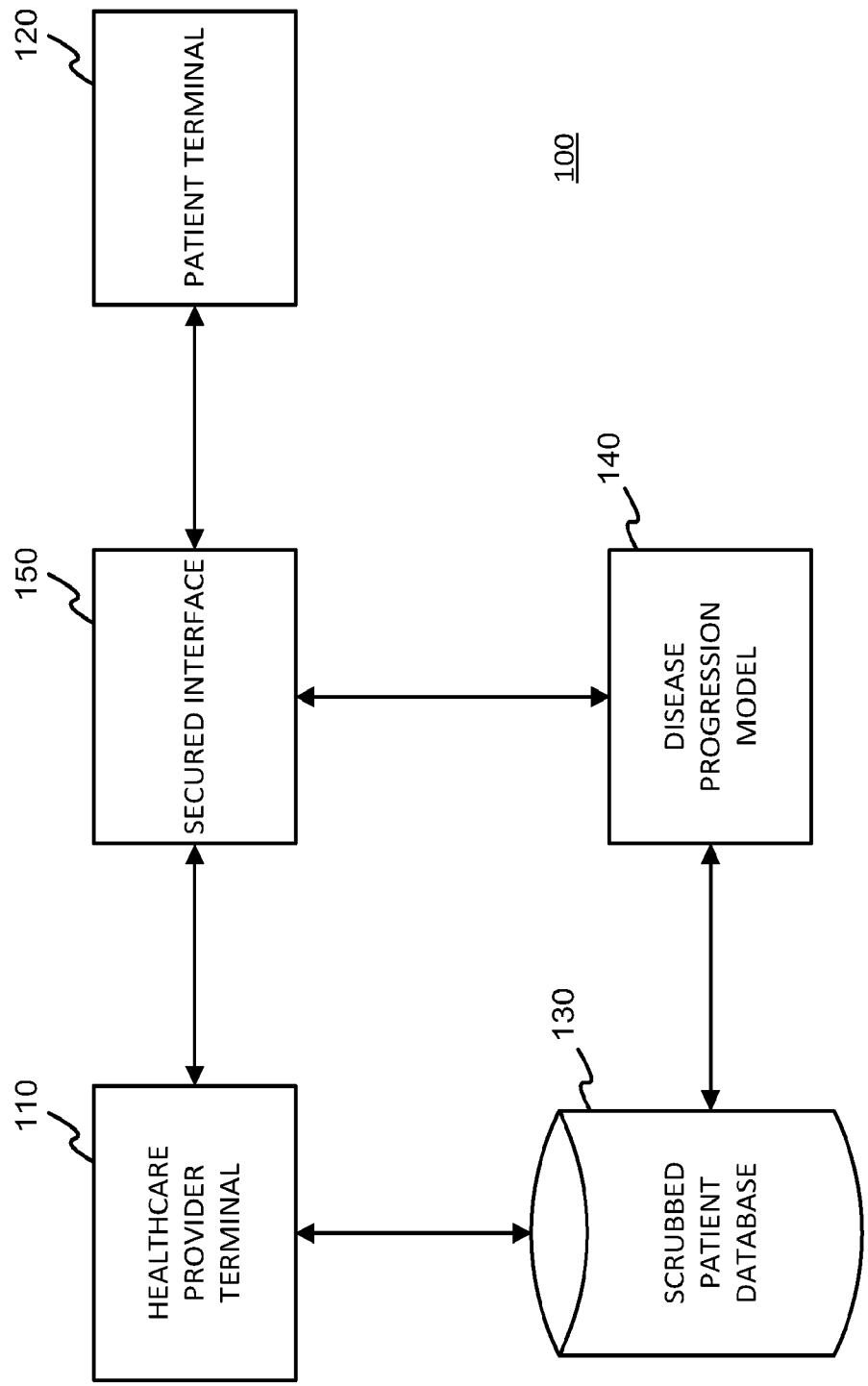
FIG. 1 is a diagram of an exemplary system that may be used to model disease progression.

Although preferred embodiments of the invention are explained in detail, it is to be understood that other embodiments are contemplated. Accordingly, it is not intended that the invention is limited in its scope to the details of construction and arrangement of components set forth in the following description or illustrated in the drawings. The invention is capable of other embodiments and of being practiced or carried out in various ways. Also, in describing the preferred embodiments, specific terminology will be resorted to for the sake of clarity.

It should also be noted that, as used in the specification and the appended claims, the singular forms "a," "an" and "the" include plural references unless the context clearly dictates otherwise. References to a composition containing "a" constituent is intended to include other constituents in addition to the one named.

Also, in describing the preferred embodiments, terminology will be resorted to for the sake of clarity. It is intended that each term contemplates its broadest meaning as understood by those skilled in the art and includes all technical equivalents which operate in a similar manner to accomplish a similar purpose.

Ranges may be expressed herein as from "about" or "approximately" or "substantially" one particular value and/or to "about" or "approximately" or "substantially" another particular value. When such a range is expressed, other exemplary embodiments include from the one particular value and/or to the other particular value.

Herein, the use of terms such as "having," "has," "including," or "includes" are open-ended and are intended to have the same meaning as terms such as "comprising" or "comprises" and not preclude the presence of other structure, material, or acts. Similarly, though the use of terms such as "can" or "may" are intended to be open-ended and to reflect that structure, material, or acts are not necessary, the failure to use such terms is not intended to reflect that structure, material, or acts are essential. To the extent that structure, material, or acts are presently considered to be essential, they are identified as such.

It is also to be understood that the mention of one or more method steps does not preclude the presence of additional method steps or intervening method steps between those steps expressly identified. Moreover, although the term "step" may be used herein to connote different aspects of methods employed, the term should not be interpreted as implying any particular order among or between various steps herein disclosed unless and except when the order of individual steps is explicitly required.

The components described hereinafter as making up various elements of the invention are intended to be illustrative and not restrictive. Many suitable components that would perform the same or similar functions as the components described herein are intended to be embraced within the scope of the invention. Such other components not described herein can include, but are not limited to, for example, similar components that are developed after development of the presently disclosed subject matter.

To facilitate an understanding of the principles and features of the invention, various illustrative examples are explained below. In particular, the presently disclosed subject matter is described in the context of being a disease progression model. The present invention, however, is not so limited, and can be applicable in other contexts. For example and not limitation, some examples of the present invention may improve other disease progression models. These examples are contemplated within the scope of the present invention. Accordingly, when the present invention is described in the context of a disease progression model, it will be understood that other examples can take the place of those referred to.

The disclosed systems and methods for disease progression modeling may have applicability with any disease, including degenerative diseases. In one example, for instance, the disclosed systems and methods may facilitate training a disease progression model having a two dimensional ("2D") continuous-time ("CT") hidden Markov model ("HMM") so that it can accurately model disease progression. In another example, the disclosed systems and methods may determine a disease state transition path when there is an extended time between a patient's visits to a healthcare provider or rapid disease degeneration for the patient. In yet another example, the disclosed systems and methods may detect when a transition between disease states is faster than other transitions. The disclosed systems and methods may predict future disease states for a patient and/or determine an expected time to transition to a future disease state, thereby scheduling a next appointment with a patient's healthcare provider. Further, the disclosed systems and methods may diagnose diseases, disease progression rates, and other attributes.

Referring now to the figures, wherein like reference numerals represent like parts throughout the views, examples will be described in detail.

FIG. 1 shows a diagram of an exemplary system configured to perform one or more software processes that, when executed, model disease progression for a patient. The components and arrangements shown in FIG. 1 are not intended to limit the disclosed examples as the components used to implement the disclosed processes and features may vary.

In accordance with disclosed examples, a disease progression modeling system 100 may include a healthcare provider terminal 110, a patient terminal 120, a scrubbed patient database 130, a disease progression model 140, and a secured interface 150. Healthcare provider terminal 110 may be connected to disease progression model 140 directly or via secured interface 150 to provide patient data or receive outputs from disease progression model 140. Healthcare provider terminal 110 may be connected to scrubbed patient database 130 to provide scrubbed patient data. Disease progression model 140 may be connected to scrubbed patient database 130 to receive the scrubbed patient data for training and/or updating disease progression model 140. It is contemplated that each component in disease progression modeling system 100 may be directly connected or in communication over a network. Other components known to one of ordinary skill in the art may be included in disease progression modeling system 100 to process, transmit, provide, and receive information consistent with the disclosed examples.

Healthcare provider terminal 110 may receive, send, record, and store patient disease data relating to one or more patients. For example, a doctor associated with healthcare provider terminal 110 may treat a patient for a disease and record patient health information including test results and disease progression data. The healthcare provider associated with healthcare provider terminal 110 may be any type or number of healthcare provider, such as, for example, an individual doctor or nurse, a doctor's office, a local hospital, a regional hospital, a university clinic, or a combination thereof. Although the example of disease progression modeling is disclosed, the healthcare provider may use disease progression model 140 in any way or for any application.

Operating in communication with one or more components of disease progression modeling system 100 via direct connection or over a network, healthcare provider terminal 110 may be a computer-based system. For example, healthcare provider terminal 110 may include a general purpose or notebook computer, a mobile device with computing ability, a server, a desktop computer, tablet, smartphone, dedicated handheld device, or any combination of these computers and/or affiliated components. In one example, healthcare provider terminal 110 may be a computer system or device that is operated by a user who is a healthcare provider or associated with a healthcare provider. In another embodiment, customer terminal 110 may be a mobile computer device that is operated by a first responder at a location of injury or disease progression. Healthcare provider terminal 110 may be configured with storage that stores one or more operating systems that perform known operating system functions when executed by one or more processors. By way of example, the operating systems may include Microsoft Windows™, Unix™, Linux™, Apple™ operating systems, Personal Digital Assistant (PDA) type operating systems, such as Microsoft CE™, Android™ or other types of operating systems. Accordingly, disclosed examples may operate and function with computer systems running any type of operating system. Healthcare provider terminal 110 may also include communication software that, when executed by a processor, provides communications with a network, such as Web browser software, tablet, or smart hand held device networking software, etc. Healthcare provider terminal 110 may be a device that executes mobile applications, such as a tablet or mobile device.

Patient terminal 120 may allow a patient or persons associated with a patient to receive, send, record, and store patient data, including confidential patient data, and receive outputs from disease progression model 140. A patient associated with patient terminal 120 may include any type of patient for any disease, injury, or affliction. Further, the disclosed examples are applicable to existing patients, and are not limited to new or potential patients. Patient terminal 120 may be a computer-based system including computer system components, such as one or more servers, desktop computers, workstations, tablets, hand held computing devices, memory devices, and/or internal network(s) connecting the components.

Scrubbed patient database 130 may allow any number of healthcare providers to provide patient data. Scrubbed patient database 130 may receive patient data that has already been scrubbed free of confidential patient information and/or may include any type of filters or algorithms to scrub received patient data. The scrubbed patient database 130 can comply with HIPAA (Health Insurance Portability and Accountability Act). Scrubbed patient database 130 may be stored by a healthcare provider, with the disease progression model, by a third party database manager, or in a data cloud accessible over a network. Scrubbed patient database 130 may be a computer-based system including computer system components, such as one or more servers, desktop computers, workstations, tablets, hand held computing devices, memory devices, and/or internal network(s) connecting the components. Scrubbed patient database 130 may include one or more memory devices that store data and instructions used to perform one or more features of the disclosed examples. Memory devices may also include any combination of one or more databases controlled by memory controller devices (e.g., server(s), etc.) or software, such as document management systems, Microsoft SQL databases, SharePoint databases, Oracle™ databases, Sybase™ databases, or other relational databases. Memory may also include software components that, when executed by a processor, perform one or more processes consistent with the disclosed examples.

Scrubbed patient database 130 may be configured to identify and/or store sorted patient data. Sorted patient data may include any subset of patient data stored within scrubbed patient database 130. For example, sorted patient data may include patient health information and/or disease progression data related to patients having a particular attribute such as having glaucoma, having 20/20 vision, or between the ages of 45 and 50. Scrubbed patient database 130 may filter received patient data to obtain stored patient data or may receive filtered patient data from healthcare provider terminal 110. Scrubbed patient database 130 may receive requests for patient data or sorted patient data and send the requested data to disease progression model 140.

Disease progression model 140 may receive data related to a particular patient from healthcare provider terminal 110 and patient terminal 120 via secured interface 150 and receive scrubbed patient data for training from scrubbed patient database 130. Upon receiving data, disease progression model 140 may process and make one or more determinations based on the data to, for example, model disease progression, identify fast transitions between disease states, predict future disease states, schedule future healthcare provider appointments based on anticipated disease progression, and diagnose diseases. Disease progression model 140 may output its determinations, analysis, and/or resulting data to healthcare provider terminal 110 and/or patient terminal 120 via secured interface 150. In some examples, disease progression model 140 may request patient data or sorted patient data from scrubbed patient database 130. Disease progression model 140 may be a computer-based system including computer system components, such as one or more servers, desktop computers, workstations, tablets, hand held computing devices, memory devices, and/or internal network(s) connecting the components.

Secured interface 150 may comprise any type of computer networking arrangement used to exchange data on a secure platform. Secured interface 150 may be a computer-based system including computer system components, such as one or more servers, desktop computers, workstations, tablets, hand held computing devices, memory devices, and/or internal network(s) connecting the components. Secured interface 150 may require login credentials from healthcare provider terminal 110 and/or patient terminal 120 to allow terminals 110 and 120 to communicate with disease progression model 140. For example, secured interface 150 may require users to login via an application programmable interface on a website accessed via the Internet, a secured private data network, or a secured virtual private network using a public network such as the Internet. Secured interface 150 may store data from healthcare provider terminal 110, patient terminal 120, and/or disease progression model 140, and allow access of the stored information after secured login. It is contemplated that alternative security software and/or devices may be used to ensure the safekeeping of confidential patient data.

Figure 2:
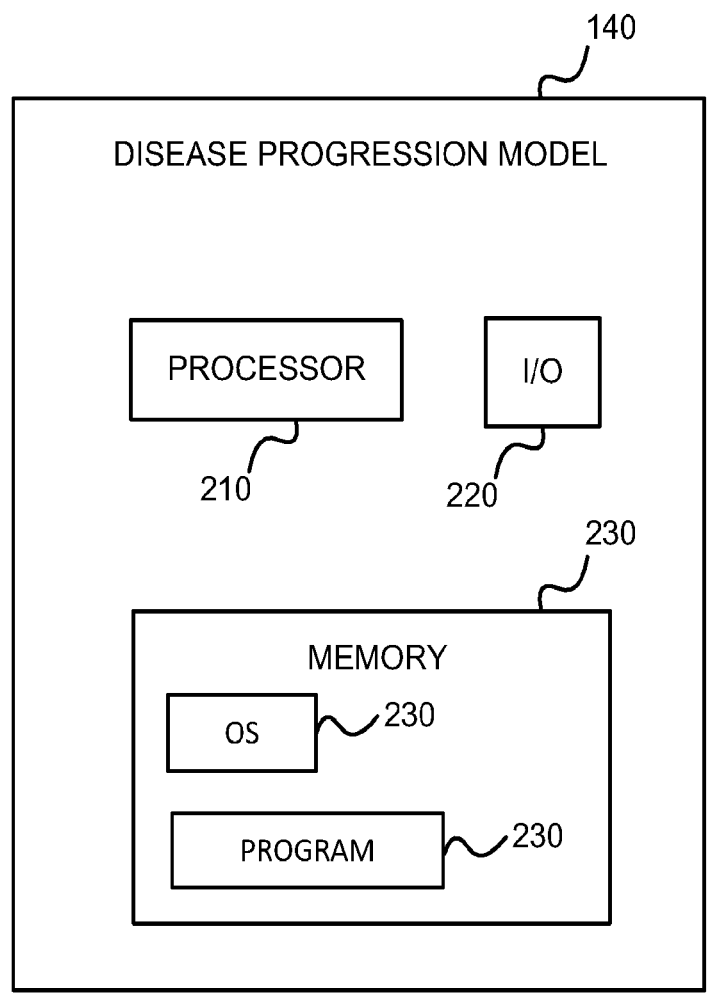
FIG. 2 is a component diagram of an exemplary disease progression model.

Disease progression model 140 is shown in more detail in FIG. 2. Healthcare provider terminal 110 and patient terminal 110 may have a similar structure and components that are similar to those described with respect to disease progression model 140. As shown, disease progression model 140 may include a processor 210, an input/output ("I/O") device 220, a memory 230 containing an operating system ("OS") 240 and a program 250. For example, disease progression model 140 may be a single server or may be configured as a distributed computer system including multiple servers or computers that interoperate to perform one or more of the processes and functionalities associated with the disclosed examples.

Processor 210 may be one or more known processing devices, such as a microprocessor from the Pentium™ family manufactured by Intel™ or the Turion™ family manufactured by AMD™. Processor 210 may constitute a single core or multiple core processor that executes parallel processes simultaneously. For example, processor 210 may be a single core processor that is configured with virtual processing technologies. In certain examples, processor 210 may use logical processors to simultaneously execute and control multiple processes. Processor 210 may implement virtual machine technologies, or other similar known technologies to provide the ability to execute, control, run, manipulate, store, etc. multiple software processes, applications, programs, etc. In another embodiment, processor 210 may include a multiple-core processor arrangement (e.g., dual or quad core) that is configured to provide parallel processing functionalities to allow server 200 to execute multiple processes simultaneously. One of ordinary skill in the art would understand that other types of processor arrangements could be implemented that provide for the capabilities disclosed herein.

Disease progression model 140 may include one or more storage devices configured to store information used by processor 210 (or other components) to perform certain functions related to the disclosed examples. In one example, disease progression model 140 may include memory 230 that includes instructions to enable processor 210 to execute one or more applications, such as server applications, network communication processes, and any other type of application or software known to be available on computer systems. Alternatively, the instructions, application programs, etc. may be stored in an external storage or available from a memory over a network. The one or more storage devices may be a volatile or non-volatile, magnetic, semiconductor, tape, optical, removable, non-removable, or other type of storage device or tangible computer-readable medium.

In one example, disease progression model 140 includes memory 230 that includes instructions that, when executed by processor 210, perform one or more processes consistent with the functionalities disclosed herein. Methods, systems, and articles of manufacture consistent with disclosed examples are not limited to separate programs or computers configured to perform dedicated tasks. For example, disease progression model 140 may include memory 230 that may include one or more programs 250 to perform one or more functions of the disclosed examples. Moreover, processor 210 may execute one or more programs 250 located remotely from digital blank check system 100. For example, disease progression modeling system 100 may access one or more remote programs 250, that, when executed, perform functions related to disclosed examples.

Memory 230 may include one or more memory devices that store data and instructions used to perform one or more features of the disclosed examples. Memory 230 may also include any combination of one or more databases controlled by memory controller devices (e.g., server(s), etc.) or software, such as document management systems, Microsoft SQL databases. SharePoint databases, Oracle™ databases, Sybase™ databases, or other relational databases. Memory 230 may include software components that, when executed by processor 210, perform one or more processes consistent with the disclosed examples.

Disease progression model 140 may also be communicatively connected to one or more memory devices (e.g., databases (not shown)) locally or through a network. The remote memory devices may be configured to store information and may be accessed and/or managed by disease progression model 140. By way of example, the remote memory devices may be document management systems, Microsoft SQL database, SharePoint databases, Oracle™ databases, Sybase™ databases, or other relational databases. Systems and methods consistent with disclosed embodiments, however, are not limited to separate databases or even to the use of a database.

Disease progression model 140 may also include one or more I/O devices 220 that may comprise one or more interfaces for receiving signals or input from devices and providing signals or output to one or more devices that allow data to be received and/or transmitted by disease progression model 140. For example, disease progression model 140 may include interface components, which may provide interfaces to one or more input devices, such as one or more keyboards, mouse devices, and the like, that enable disease progression model 140 to receive data from one or more users (such as healthcare provider terminal 110).

Disease progression model 140 may be configured to store and operate a two dimensional ("2D") continuous-time ("CT") hidden Markov model (HMM). An HMM statistically models a system assumed to be a Markov process with hidden (i.e., unobserved) states. In an HMM, the state is not visible, but an output dependent on the state is visible. For example, while it may be unknown the exact disease stage that a patient may be in, the patient may be tested or measured and those results may be analyzed to assess the hidden disease state.

Unlike a discrete time HMM, a CT HMM allows for irregular data points to be entered into the model. In other words, a discrete time HMM requires data at set time intervals to properly function. In the real world of medical treatment, patients and their scheduled appointments rarely, if ever, conform to the regularity required for a discrete time HMM. CT HMM allows for patients to be monitored at irregular intervals. By not requiring patients to be monitored regularly, disease progression model 140 may more accurately evaluate patients who cannot or do not visit a health provider at regular time intervals based on a lack of time, monetary resources, and/or changing schedules. As such, a CT HMM may be used to model disease progression for a patient who was tested by a health provider for three months in a row and then waited two years before being tested again by the healthcare provider. An HMM may make the assumption that transitions between disease states take place at one or more of the sample times corresponding to regularly-sampled data. In contrast, a CT HMM may permit transitions in disease states to occur at any continuous time value, and can utilize the irregularly sampled data to infer the actual transition time.

In CT HMMs, however, it may be more challenging to accomplish parameter learning and inference than for discrete time HMMs. For instance, the use of matrix exponential terms in CT HMMs data likelihood function may make it hard to derive a closed form optimization formula for efficient learning, if without restricted assumptions. Therefore, CT HMM is generally used with very small model structure in medicine, such as a model with only a single dimension of disease progression that is divided into 3 to 5 states. It is contemplated that disease progression model 140 may develop a 2D disease state structure for modeling disease progression along with two dimensions of disease progression, and use an efficient CT HMM parameter learning algorithm such that CT HMM learning and inference with such a corresponding large-scale state space is practical.

Figure 3:
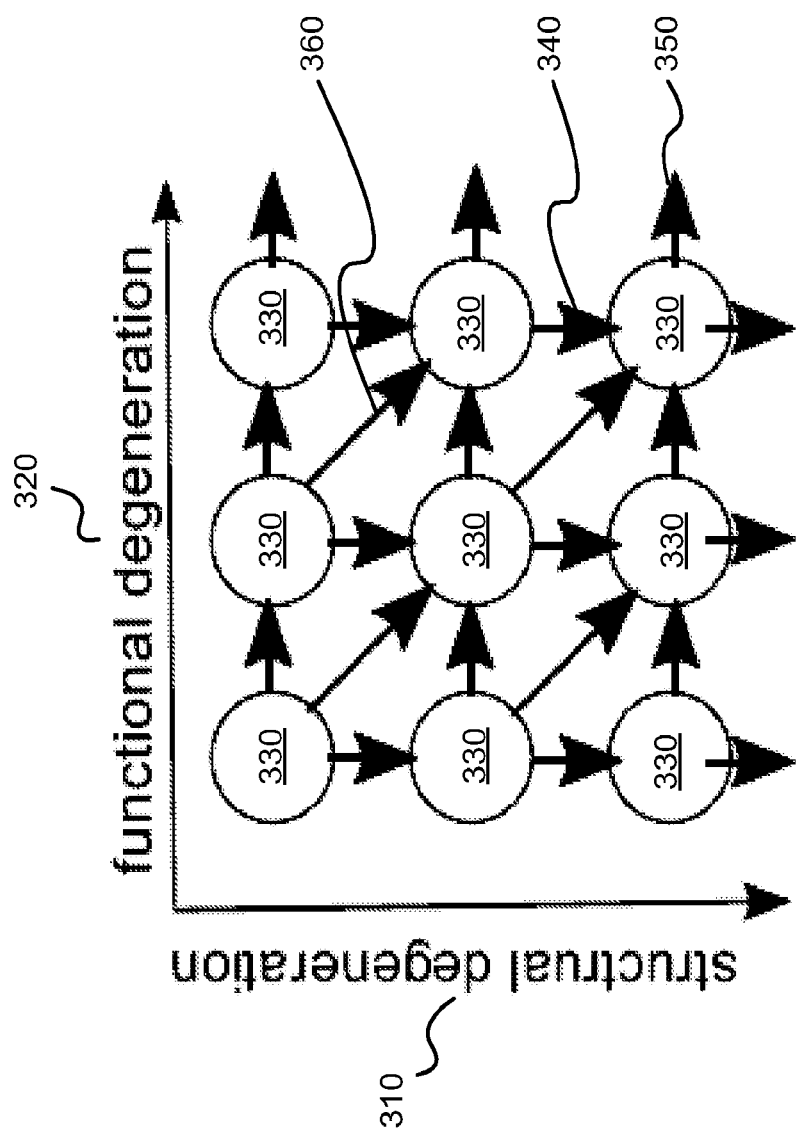
FIG. 3 is a diagram of an exemplary model having a plurality of disease states.

FIG. 3 depicts an example model having a plurality of 2D disease states 330. In contrast to binary disease states (e.g., having or not having a disease), disease states 330 capture multiple stages of a disease and may be used to show disease progression. The disease states 330 are hidden, but can be hypothesized or estimated based on measurements and other disease indicators, which can be used as the axis as illustrated. By having two dimensions, the disease states 330 can provide a more holistic view of a stage of a disease. While disclosed disease states 330 are discussed with respect to glaucoma, it is contemplated that disease states 330 may apply to any disease, particularly any degenerative disease (e.g., Alzheimer's, Parkinson's, etc.).

In assessing glaucoma, it may be important to consider both structural degeneration data 310 and functional degeneration data 320. Structural degeneration data 310 may include any test results or measurements related to the structure of a human or animal anatomy itself and may be acquired using specialized equipment. In glaucoma, for example, an optical coherence tomography ("OCT") device may be used to measure structural degeneration data 310 such as total retinal thickness, retinal nerve fiber thickness, ganglion cell layer thickness, ganglion cell-inner plexiform layer thickness, ganglion cell complex thickness, rim area, rim volume, cup to disc ("C/D") ratio, and cup volume. A scanning laser ophthalmoscopy ("SLO") device may be used to measure structural degeneration data 310 such as retinal nerve fiber thickness, rim area, rim volume, C/D ratio, and cup volume. Further, a scanning laser polarimetry ("SLP") device may be used to measure structural degeneration data 310 such as retinal nerve fiber thickness. It is contemplated that disease progression model 140 and/or other components of disease progression modeling system 100 may be in communication with one or more structural measurement devices.

Functional degeneration data 320 may include any test results or measurements related to a human or animal's functional performance and may be acquired using specialized tests and equipment. In glaucoma, for example, a visual field test (for standard automated perimetry) may be used to measure functional degeneration data 320 such as mean deviation, pattern standard deviation, and visual field index. A pattern electroretinogram ("ERG") may be used to measure functional degeneration data 320 such as amplitude. A multifocal ERG may be used to measure functional degeneration data 320 such as amplitude and phase at 103 points. Further, a multifocal visual evoked potential ("VEP") device may be used to measure fu functional degeneration data 320 such as amplitude and phase at multiple points. It is contemplated that disease progression model 140 and/or other components of disease progression modeling system 100 may be in communication with one or more functional measurement devices.

Disease states 330 may be selected in a variety of ways. The number of disease states 330 may depend on the variations within the patient progression data related to a plurality of patients having a disease or another attribute. For example, with a less complex disease, nine disease states 330 may be used, including three different ranges of structural degeneration data 310 and three different ranges of functional degeneration data 320. With more complex diseases, however, 100 or more disease states 300 may be used. It is contemplated that four or more disease states 330 may be used and that disease states 330 may have a different number of structural degeneration data 310 and functional degeneration data 320 ranges (e.g., two rows of structural degeneration data 310 ranges and 4 columns of functional degeneration data 320 ranges).

In some examples, the minimum and maximum structural degenerative data 310 and functional degenerative data 320 values may be defined based on the minimum and maximum measurements in the patient progression data. Within those minimum and maximum values, ranges associated with each disease state 330 may be associated with high concentrations of measurements in the patient progression data. When there is not much data available, the ranges associated with each disease state 330 may be associated with at least one measurement in the patient progression data. In other examples, ranges associated with each disease state 330 may be evenly divided between the minimum and maximum values. Further, it is contemplated that disease states 330 may be associated with known disease stages (e.g., stage three lung cancer) and the ranges associated with each disease state 330 may reflect measurements associated with the known disease stages. In another example, the modeled disease states may not have an equivalent clinical disease state. As use of the model progresses, the modeled disease states may be categorized to coincide with a clinical counterpart, or the clinical states may be modified to closer track the disease states determined by the model.

As shown in FIG. 3, each disease state 330 may be non-overlapping and have a multiple adjacent disease states 330. Each disease state 330 may have one or more transition paths 340, 350, 360 to transition to another disease state 330 as time progresses. For example, in degenerative diseases, transition paths may be limited to a structural degeneration transition 340 (i.e., patient degenerates structurally only), a functional degeneration transition (i.e., patient degenerates functionally only), and a structural and functional degeneration transition 360 (i.e., patient degenerates both structurally and functionally). It is contemplated, however, that other transition paths may be available for other diseases.

Each transition path 340, 350, 360 may be associated with a probability of transitioning from one disease state 330 to another. Each probability may be determined based on measurements in the patient progression data stored in scrubbed patient database 130. For example, at any particular disease state 330, there may be a 20% probability that the disease progresses along transition path 340, a 30% probability that the disease progresses along transition path 350, and a 50% probability that the disease progresses along transition path 360. As more data is collected, the accuracy in determining these probabilities may increase.

Figure 4:
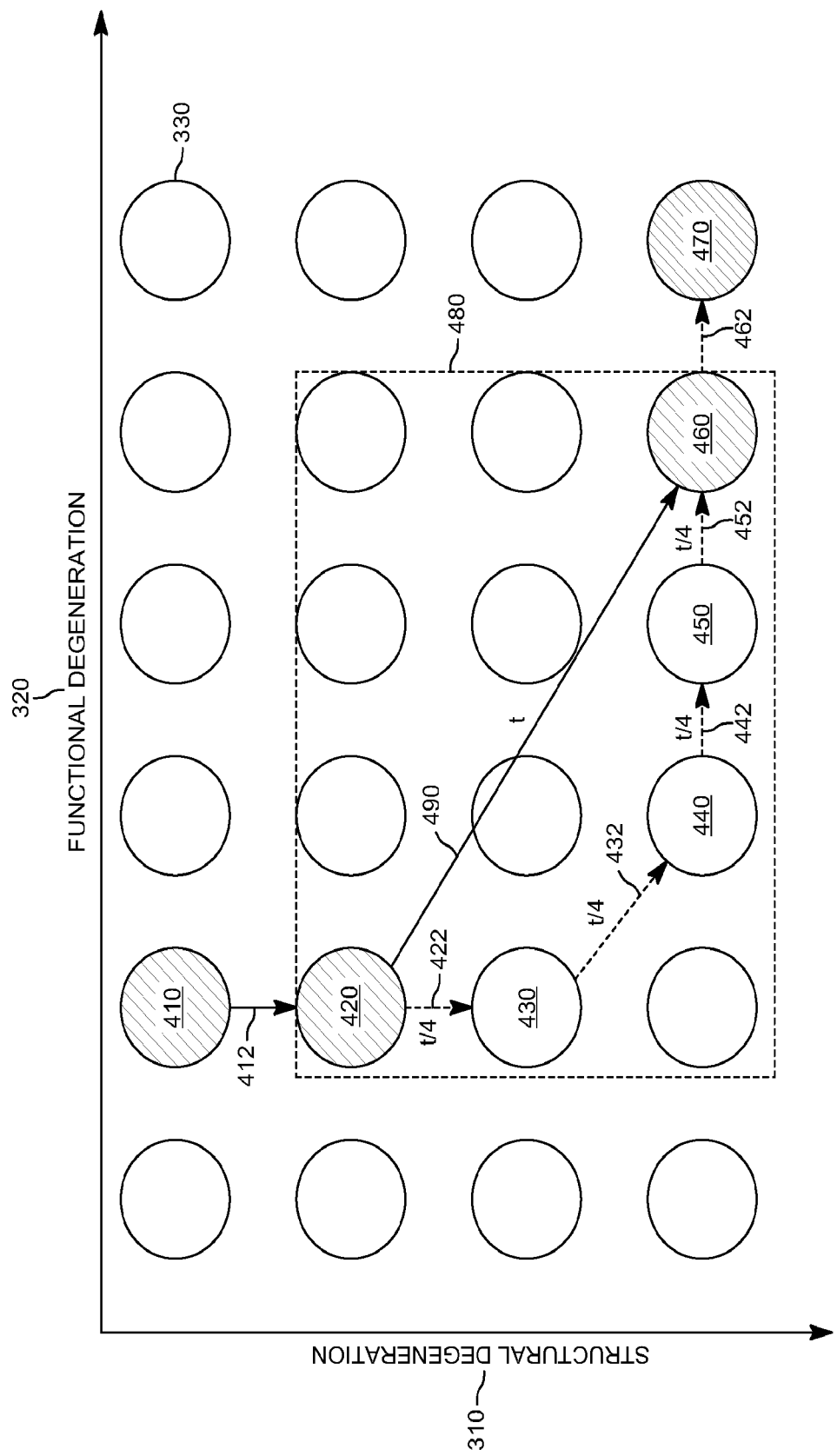
FIG. 4 is a diagram of an exemplary most probable path between two non-adjacent disease states.

FIG. 4 depicts an example of an individual patient's disease progression. As shown, the patient's initial structural and/or functional measurements may indicate that the patient is in a first disease state 410. At time progresses, the disease structurally degenerates along first transition path 412 and the patient's structural and/or functional measurements may indicate that the patient is in a second disease state 420. Then, when the patient is sequentially tested, the disease structurally and functionally degenerates along intermediary transition path 490 such that the patient's structural and/or functional measurements may indicate that the patient is in a sixth disease state 460. Because second disease state 420 and sixth disease state 460 are non-adjacent disease states 330, it is unclear how the disease progressed between them. Determining the most probable path of the patient's disease progression may be important to disease diagnosis and treatment.

Using disease progression model 140, it may be possible to determine a most probable path of the disease progression between two non-adjacent states (e.g., second disease state 420 and sixth disease state 460), which are identified by a gap box 480. For example, disease progression model 140 may determine that the patient's disease structurally degenerated along a second transition path 422 to a third disease state 430, structurally and functionally degenerated along a third transition path 432 to a fourth disease state 440, functionally degenerated along a fourth transition path 442 to a fifth disease state 450, and functionally degenerated along a fifth transition path 452 to sixth disease state 460. It is important to note that discrete time HMMs may be unable to handle large gaps between disease states 330 along a disease progression path, which may often be due to irregular time spans between patient testing, because the discrete time HMM requires regular patient testing intervals.

When the patient was sequentially tested after being in sixth disease state 460, the disease functionally degenerated along sixth transition path 462 such that the patient's structural and/or functional measurements may indicate that the patient is in a seventh disease state 470. While in seventh disease state 470, disease progression model 140 may be used to predict a most probable future state using the known transition probabilities.

Figure 5:
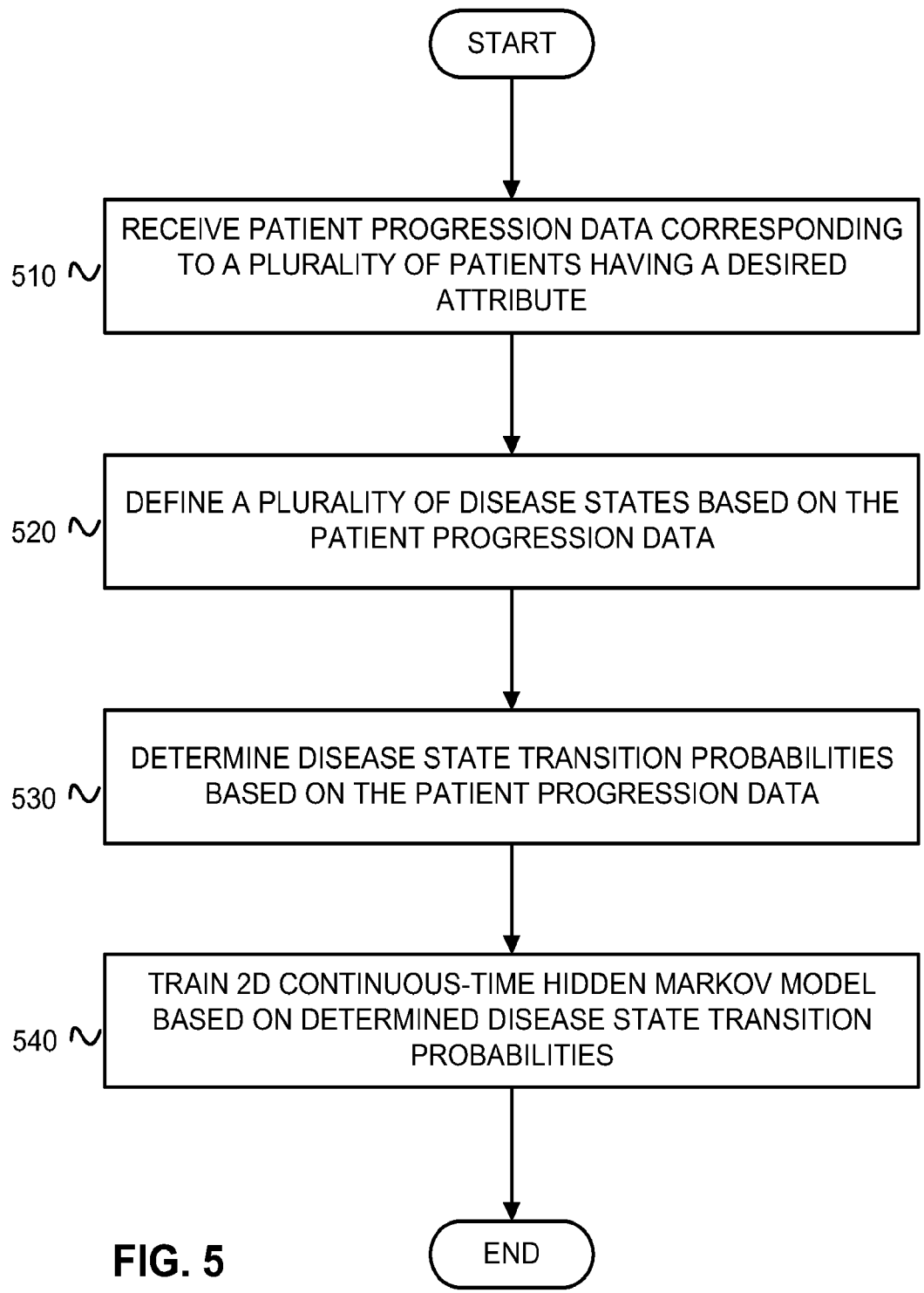
FIG. 5 is a flowchart of an exemplary method for training a disease progression model.

FIG. 5 shows an exemplary process for disease progression model training 500. As shown, disease progression model 140 may receive patient progression data 510 corresponding to a plurality of patients having a desired attribute from scrubbed patient database 130. In some examples, patients having a desired attribute may include patients having glaucoma. In other examples, the attribute may include having glaucoma with a particular progression rate. Further, in other examples, the attribute may include not having glaucoma.

After receiving the patient progression data 510, disease progression model 140 may define a plurality of disease states 520 based on the patient progression data. As shown in FIGS. 3 and 4, for example, disease progression model 140 may define 9, 24, or more disease states 330 corresponding to concentrations within the patient progression data.

In one example, once disease progression model 140 has defined the plurality of disease states 520, it may determine disease state transition probabilities 530 based on the patient progression data. In other words, based on trends of disease progression in the patient progression data, disease progression model 140 may determine the probability of degenerating structurally, functionally, or both structurally and functionally to the next disease state 330.

Disease progression model 140 may train a 2D CT HMM 540 based on the determined disease state transition probabilities. For example, the HMM may be structured using data for a plurality of patients, where each patient i has $n_i$ visits, consisting of irregularly spaced visiting times $(t_{i1}, \ldots, t_{in_i})$, and corresponding observational data $(o_{i1}, \ldots, oi_{ni})$. The hidden states for the data may be denoted as $(s_{i1}, \ldots, si_{ni})$ where each state is from a discrete set S. The observation o may be generated conditionally on the hidden state s based on the data emission probability $p(o|s)$.

The hidden states (e.g., intermediary disease states 430, 440, and 450 in FIG. 4) may evolve with time as an unobserved Markov process. The next disease state that the patient's disease transitions to, and the timing of that transition, are governed by a set of transition intensities (i.e., probabilities), $q_{rs}$, for each pair of states r (e.g., second disease state 420 in FIG. 4) and s (e.g., sixth disease state 460 in FIG. 4). Each transition intensity represents the instantaneous risk of moving from disease state r to disease state s, and is defined as:

$$q_{rs} = lim_{\delta t \to \infty} p(S(t+\delta t)=s|S(t)=r)/\delta t$$

where S(t) represents disease state 330 at time t. These transition intensities form a matrix Q ("instantaneous transition intensity matrix"), whose rows are defined to sum to zero, with the diagonal entries set to $q_{rr}=-\Sigma_{s \neq r} q_{rs}$. The average sojourn time (i.e., a single period of occupancy) in disease state r is given by $-1/q_{rr}$. The probability that the next transition from disease state r to disease state s is $-q_{rs}/q_{rr}$t, for $r \neq s$.

The transition probability matrix with time parameter t is denoted as P(t), and may be computed by taking the matrix exponential of Q: $P(t)=e^{tQ}$. The (r, s) entry of P(t), denoted as $p_{rs}(t)$, is the probability of being in state s at instant ($t_0$+t) in the future, given that the state at time $t_0$ is r. It is contemplated that $p_{rs}(t)$ may be non zero when there is a transition path from disease state r to disease state s in the HMM even if $q_{rs}$ is 0.

To efficiently estimate the parameters for the HMM, disease progression model 140 may assume that when the identified states for two consecutive visits are adjacent (i.e., have a $q_{rs}$ link), the disease state transition takes place exactly at the visiting time of the second visit. This assumption may be valid when the duration between consecutive visits is not long. It is contemplated, however, that other assumptions may be used to define the disease state transition time(s). In some examples, disease progression model 140 may use a hard expectation-maximization algorithm conceptually similar to a Viterbi-Training algorithm.

The optimization problem for the HMM may be $max_s f(S, O|\lambda)$ for iteratively updating the HMM parameter $\lambda$. In an E-step, given the current $\lambda$, disease progression model 140 may determine the most probable path S* for each data sequence $O=o_1, o_2, \ldots, o_n$ with visiting time $T=t_1, t_2, \ldots, t_n$ by Viterbi decoding:

$$p(S^*,O|\lambda) = max_{S^*=s_1,s_2,\ldots,s_n}\{\pi(s_1)p(o_1|s_1)\Pi_{k=2}^n p(o_k|s_k)P_{s_{k-1},s_k}(t_k-t_{k-1})\}$$

where $\pi(s)$ is the initial state probability, p(o|s) is the data emission probability, and $P_{r,s}(t)$ is the entry of transition probability matrix P(t) computed from Q.

In the decoded state sequence S*, there may be two consecutive disease states r, s that are non-adjacent (i.e., $q_{rs}$ is 0), which may occur when the time gap between the two visits is long or there is very rapid degeneration. Disease progression model 140 may also utilize this transition information to help estimate $q_{ij}$ parameters, where i, j are intermediary disease states (e.g., disease states 430, 440, and 450 in FIG. 4) in the path between disease states r and s (e.g., disease states 420 and 460 in FIG. 4). To determine the most probable path $S_{rs}$ between disease states r, s, disease progression model 140 may require that the one or more intermediary states be distinct and adjacent to disease state r, disease state s, and/or another intermediary disease state, and that the duration t between the two visits is divided uniformly into each intermediary disease state, as shown in FIG. 4. In some examples, this may be formulated as:

$$p(S_{rs}|L) = max_{S_{rs}=s_1,\ldots,s_l,l \in l_{rs},s_i \neq s_j,1 \leq i,j \leq l} \prod_{u=2}^{l-1} P_{s_u,s_{u+1}}\left(\frac{t}{l}\right)$$

where $l_{rs}$ is the set of all possible lengths of distinct state transition paths between disease states r and s. In some examples, the most probable path may be determined using a Viterbi algorithm.

In an M-step, disease progression model 140 may update one or more HMM parameters. For example, $N_{rs}$ may denote the number of transitions from disease state r to disease state s, and $T_r$ may represent the total time staying at disease state r from all data, computed from the results in the E-step. When the disease state transitions are assumed to happen at the visiting times, the optimized value for the Q matrix entries may be $q_{rs}=N_{rs}/T_r$ for $r \neq s$, and $q_{rr}=-\Sigma_{r \neq s} q_{rs}$. In some examples, disease progression model 140 may iteratively update the HMM by alternating between the E-step and the M-step until a substantially fixed point is reached (e.g., until one or more parameters remain substantially constant or until the most probable path remains substantially constant).

Training the HMM 540 based on the determined disease state transition probabilities may include using the above-noted equations and algorithms to determine appropriate parameters using at least a portion of the patient progression data from scrubbed patient database 130. It is contemplated that the HMM may be re-trained using a different portion of the patient progression data or a new set of patient progression data.

Figure 6:
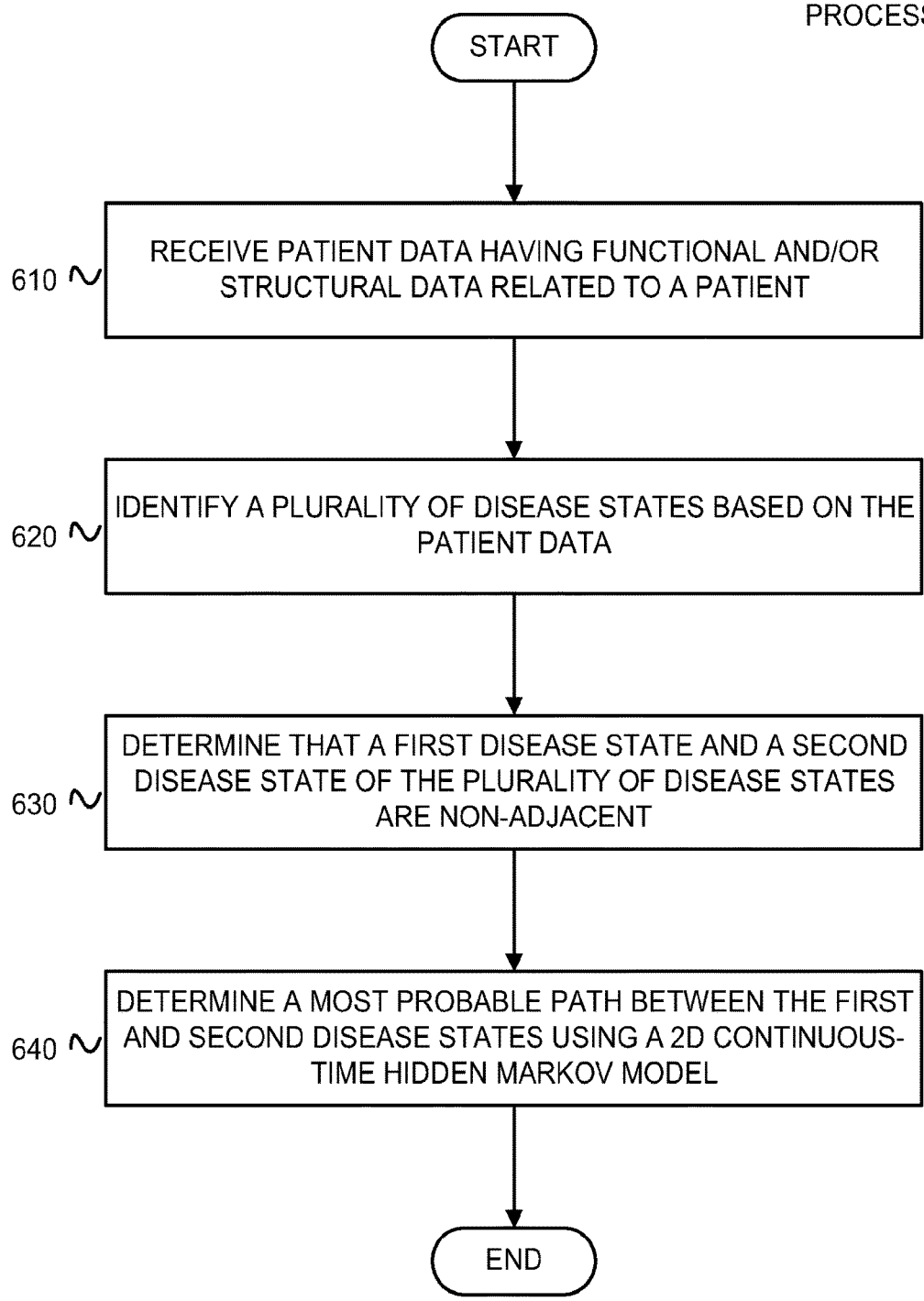
FIG. 6 is a flowchart of an exemplary process for determining a disease state transition path.

FIG. 6 shows an example of a disease state transition path determination process 600. Disease progression model 140 may receive patient data 610 having structural degeneration data 310 and/or functional degeneration data 320 related to a patient. Disease progression model 140 may receive the patient data directly from healthcare provider terminal 110 and/or patient terminal 120 or indirectly from healthcare provider terminal 110 and/or patient terminal 120 via secure interface 150. The patient data may include structural degeneration data 310 and/or functional degeneration data 320 for an individual patient at two or more points in time.

After receiving patient data 610, disease progression model 140 may identify a plurality of disease states 620 based on the patient data. For example, when the structural degeneration data 310 and/or the functional degeneration data 320 in the patient data falls into a range associated with a particular disease state 330, disease progression model 140 may identify that the patient was in that disease state 330 at the time of the visit and/or measurement. Then, disease progression model 140 may identify that the patient was in other disease states 330 at the time of other visits and/or measurements.

In other examples, disease progression model 140 may iteratively receive patient data related to a single point in time and identify a particular disease state 330 associated with the patient at that point in time. As such, it is contemplated that patient data may be received in part or all at once, and may occur before, during, and after identifying step(s) 620.

As disease progression model 140 identifies a plurality of disease states 620, it may also determine that two sequential disease states of the plurality of disease states are non-adjacent (i.e., determining the location of a gap between disease states as shown by gap box 480 in FIG. 4). For example, as shown in FIG. 4, second disease state 420 is non-adjacent to sixth disease state 460, even though sixth disease state was the next sequential disease state 330 based on the patient data.

Once disease progression model 140 determines that a first disease state and a second disease state are non-adjacent (i.e., a gap is present), it may determine a most probable path between the first and second disease states using the HMM. For example, using the trained parameters, the HMM may use the patient data in its algorithms to determine the most probable path. It is contemplated that, based on the measured or suspected attribute(s) of the patient, the HMM may be trained with patient progression data from a plurality of patients having similar attribute(s), thereby improving accuracy of disease progression model 140.

In determining the most probable path 640, disease progression model 140 may iteratively update one or more parameters of the HMM until the determined most probable path remains substantially constant. For example, disease progression model 140 may iterate between the E-step and the M-step as it did during disease progression model training process 500 as shown in FIG. 5.

Disease progression model 140 may provide the determined most probable path to healthcare provider terminal 110 and/or patient terminal 120 directly or via secure interface 150. The healthcare provider associated with healthcare provider terminal 110 and/or the patient associated with patient terminal 120 may use the determined most probable path to better analyze the progression of the disease for the patient and treat the disease accordingly.

Figure 7:
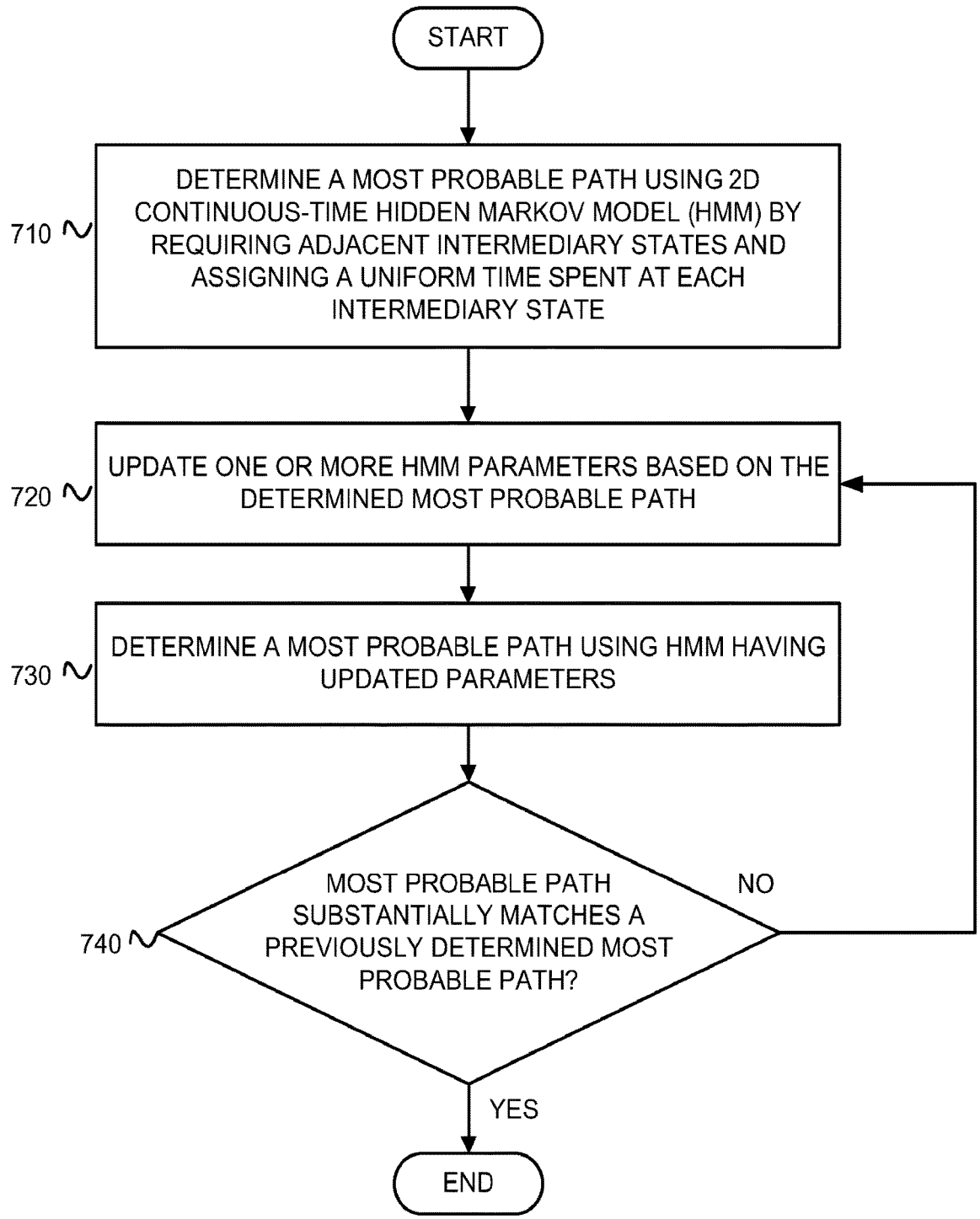
FIG. 7 is a flowchart of an exemplary method for determining a most probable path between two non-adjacent disease states.

An exemplary process for determining the most probable path 700, as shown in FIG. 7, may be used as the determining the most probable path step 640 in disease state transition path determination process 600. Disease progression model 40 may determine a most probable path 710 using the HMM by requiring that intermediary disease states (e.g., disease states 430, 440, and 450 in FIG. 4) in the path between the first and second disease states r and s (e.g., disease states 420 and 460 in FIG. 4) be distinct and adjacent to the first disease state, the second disease state, and/or another intermediary disease state, and that the duration t between the two visits is divided uniformly into each intermediary state, as shown in FIG. 4.

Disease progression model 140 may then update one or more HMM parameters 720 based on the determined most probable path until the determined most probable path remains substantially constant. For example, disease progression model 140 may perform the E-step and the M-step of the HMM as it did during disease progression model training process 500 as shown in FIG. 5.

After updating the HMM parameters 720, disease progression model 140 may determine a most probable path 730 using the HMM having updated parameter(s). Disease progression model 140 may determine whether the most probable path substantially matches 740 a previously determined most probable path. For example, the most probable path and a previously determined most probable path may match when they include the same intermediary disease states. In other examples, the most probable path and a previously determined most probable path may match when the updated HMM parameters are substantially constant to the previously used HMM parameters. For instance, the updated HMM parameters may be substantially constant to the previously used HMM parameters when there is less than a 0.01 difference between the parameters. The exact choice of criteria may depend upon the type of data being analyzed, the time available for modeling fitting, and/or other relevant criteria.

When there is a substantial match between the most probable path and the previously determined most probable path, disease progression model 140 uses the most probable path. When disease progression model 140 determines that there is no match, it may cause the HMM to iteratively update by repeating updating the parameter(s) step 720, determining a most probable path step 730, and determining whether the most probable path matches 730 a previously determined most probable path.

After determining that there is a match 740, disease progression model 140 may provide the determined most probable path to healthcare provider terminal 110 and/or patient terminal 120 directly or via secure interface 150. The healthcare provider associated with healthcare provider terminal 110 and/or the patient associated with patient terminal 120 may use the determined most probable path to better analyze the progression of the disease for the patient and treat the disease accordingly.

Figure 8:
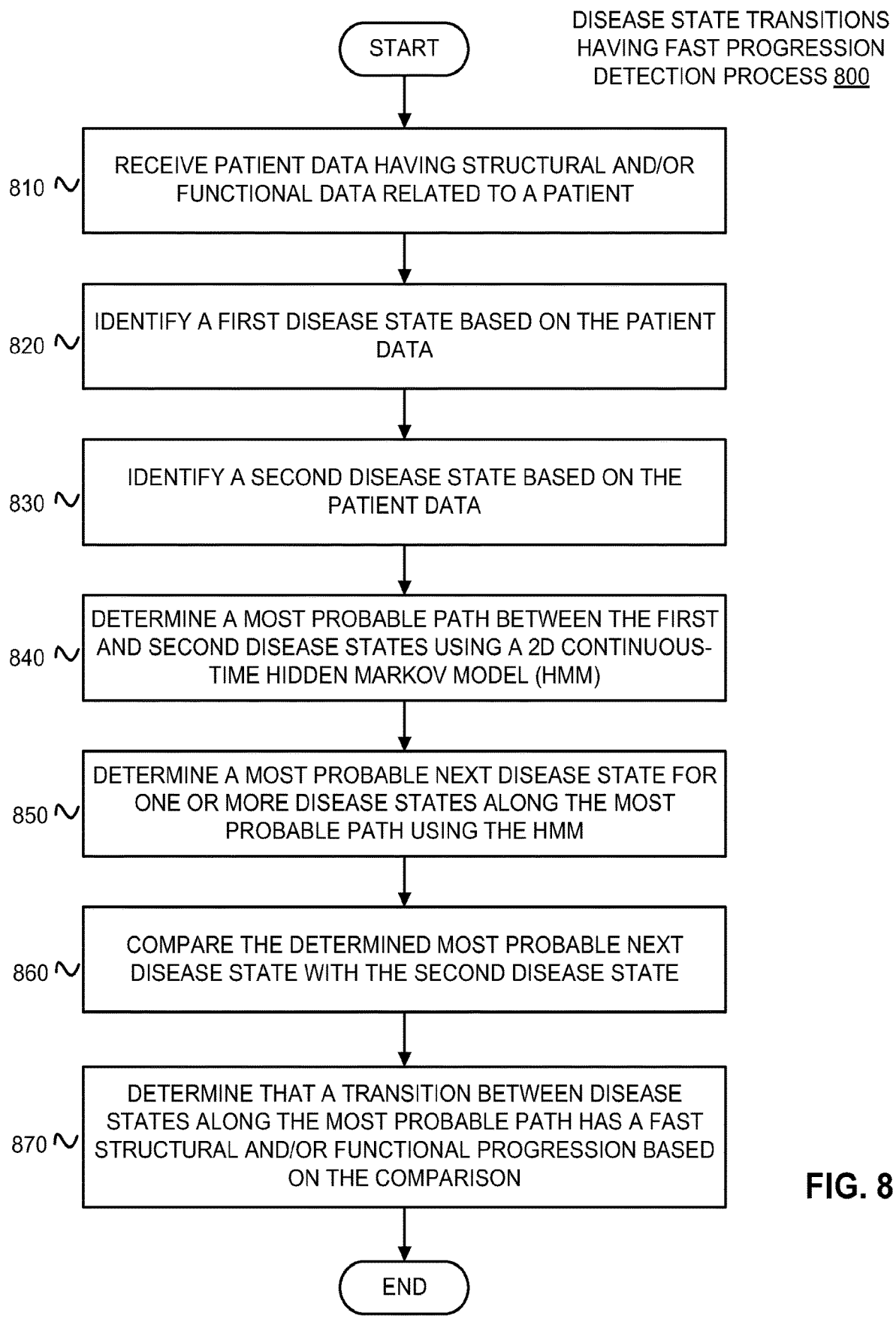
FIG. 8 is a flowchart of an exemplary process for detecting disease state transitions having fast progression.

FIG. 8 shows an exemplary process for detecting disease state transitions having fast progression 800. Disease progression model 140 may receive patient data 810 having structural degeneration data 310 and/or functional degeneration data 320 related to a patient. Disease progression model 140 may receive the patient data directly from healthcare provider terminal 110 and/or patient terminal 120 or indirectly from healthcare provider terminal 110 and/or patient terminal 120 via secure interface 150. The patient data may include structural degeneration data 310 and/or functional degeneration data 320 for an individual patient at two or more points in time.

After receiving patient data 810, disease progression model 140 may identify a first disease state 820 based on the patient data. For example, when the structural degeneration data 310 and/or the functional degeneration data 320 in the patient data falls into a range associated with disease state 420 in FIG. 4, disease progression model 140 may identify that the patient was in disease state 420 at the time of the visit and/or measurement. Then, disease progression model 140 may identify a second disease state 830 based on the patient data. For example, when the structural degeneration data 310 and/or the functional degeneration data 320 in the patient data falls into a range associated with disease state 460 in FIG. 4, disease progression model 140 may identify that the patient was in disease state 460 at the time of the visit and/or measurement. It is contemplated that the first and second disease states may be sequential and non-adjacent to one another. Further, disease progression model 140 may identify additional disease states 330 based on the patient data.

In other examples, disease progression model 140 may iteratively receive patient data related to a single point in time and identify a particular disease state 330 associated with the patient at that point in time. As such, it is contemplated that patient data may be received in part or all at once, and may occur before, during, and after identifying steps 820 and 830.

As disease progression model 140 identifies the first and second disease states in steps 820 and 830, respectively, it may also determine a most probable path 840 between the first and second disease states using the HMM. For example, using the trained parameters, the HMM may use the patient data in its algorithms to determine the most probable path. It is contemplated that, based on the measured or suspected attribute(s) of the patient, the HMM may be trained with patient progression data from a plurality of patients having similar attribute(s), thereby improving accuracy of disease progression model 140.

In determining the most probable path 840, disease progression model 140 may optionally iteratively update one or more parameters of the HMM until the determined most probable path remains substantially constant. For example, disease progression model 140 may iterate between the E-step and the M-step as it did during disease progression model training process 500 as shown in FIG. 5.

After determining the most probable path 840, disease progression model 140 may determine a most probable next disease state 850 for one or more disease states along the most probable path using the HMM. For example, at a first intermediary disease state (e.g., disease state 430 in FIG. 4), disease progression model 140 may compute the probabilities of transitioning to the next potential disease state via structural degeneration transition path 340, functional degeneration transition path 350, and structural and functional degeneration transition path 360. Further, disease progression model 140 may calculate the transition probabilities after receiving new or additional patient progression data or other patient data. It is contemplated that disease progression model 140 may determine a most probable next disease state for each disease state along the most probable path (e.g., disease states 430, 440, and 450 in FIG. 4).

After determining the most probable next disease state 850 for one or more disease states 330 along the most probable path, disease progression model 140 may compare 860 the determined most probable next disease state (or one or more of the determined most probable next disease states) with the second disease state.

Disease progression model 140 may determine that a transition between disease states along the most probable path has a fast structural and/or functional progression 870 based on the comparison 860. The determination that a transition is fast may be based on a comparison of the disease state dwelling times for a particular patient relative to the typically-observed distribution of disease state dwelling times from the plurality of patients whose observational data was used to train the model. When the dwelling time is found to be substantial lower than the typical distribution of dwelling times, the patient in question may be deemed to be a fast progressor. For example, the average disease state dwelling time may be identified for a particular transition and a patient whose dwelling time was significantly below this average could be detected as a fast progressor. One benefit of disease progression model 140 is that the detection of fast progressors may be performed automatically for all patients and all possible state transitions, leading to fast and efficient detection methods. A related procedure may be used to identify slow progressors by identifying patients whose dwellling times are longer than the typical distribution.

Disease progression model 140 may provide the determined fast transition (e.g., fast structural and/or functional progression) to healthcare provider terminal 110 and/or patient terminal 120 directly or via secure interface 150. The healthcare provider associated with healthcare provider terminal 110 and/or the patient associated with patient terminal 120 may use the determined fast transition to better analyze the progression of the disease for the patient and treat the disease accordingly. In other examples, disease progression model 140 may provide the determined fast transition to scrubbed patient database 130 for use in future patient progression data, which may be used to train the HMM for patients having a certain attribute (e.g., fast transition at a certain disease state).

Figure 9:
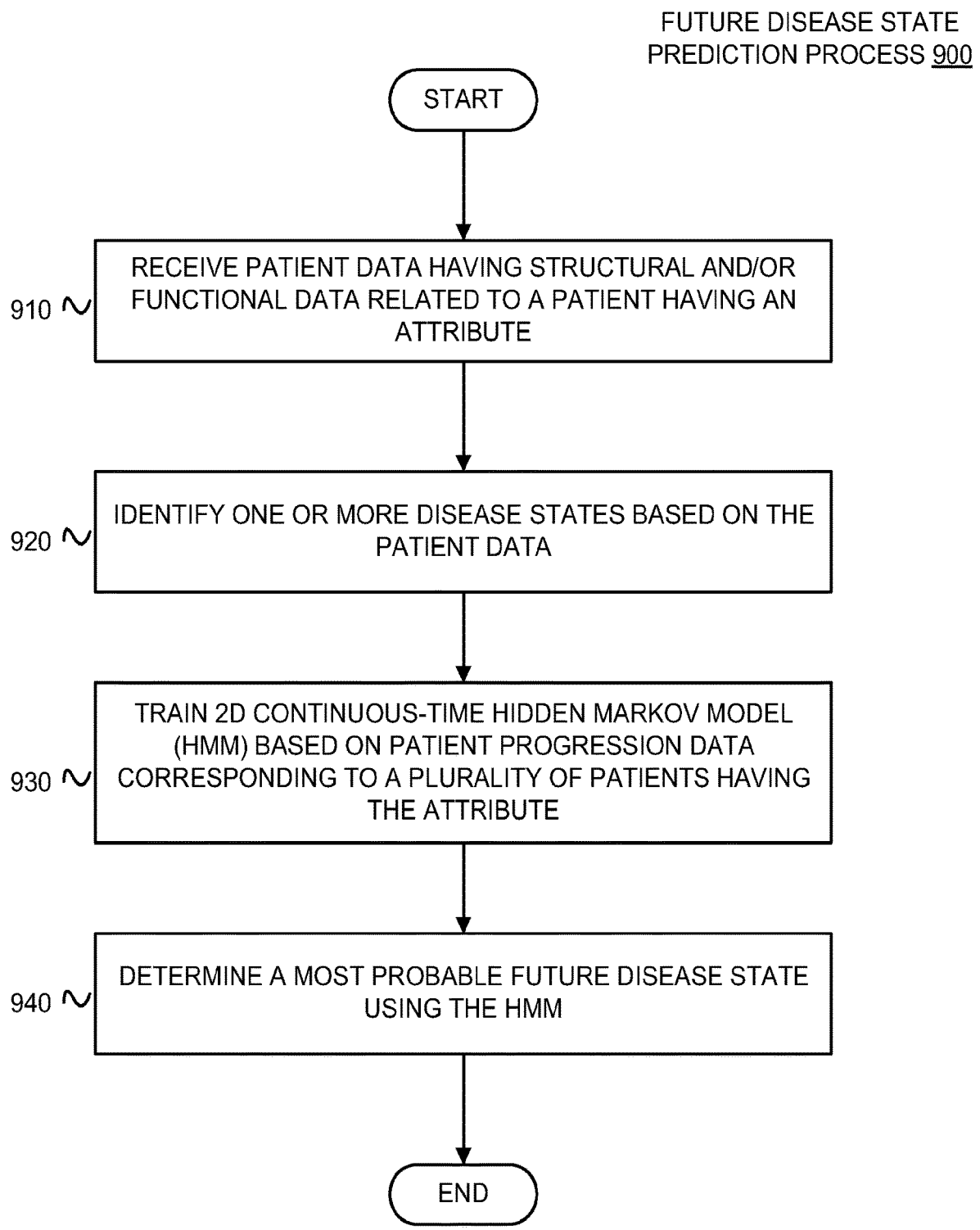
FIG. 9 is a flowchart of an exemplary method for predicting a future disease state.

FIG. 9 shows an example of a future disease state prediction process 900. Disease progression model 140 may receive patient data 910 having structural degeneration data 310 and/or functional degeneration data 320 related to a patient having an attribute. It is contemplated, however, that the patient data may not be restricted to a patient having a particular attribute. Disease progression model 140 may receive the patient data directly from healthcare provider terminal 110 and/or patient terminal 120 or indirectly from healthcare provider terminal 110 and/or patient terminal 120 via secure interface 150. The patient data may include structural degeneration data 310 and/or functional degeneration data 320 for an individual patient at two or more points in time.

After receiving patient data 910, disease progression model 140 may identify or more disease states 920 based on the patient data. For example, when the structural degeneration data 310 and/or the functional degeneration data 320 in the patient data falls into a range associated with a particular disease state 330, disease progression model 140 may identify that the patient was in that disease state 330 at the time of the visit and/or measurement. Then, disease progression model 140 may identify that the patient was in one or more other disease states 330 at different time(s) associated with other visits and/or measurements.

In other examples, disease progression model 140 may iteratively receive patient data related to a single point in time and identify a particular disease state 330 associated with the patient at that point in time. As such, it is contemplated that patient data may be received in part or all at once, and may occur before, during, and after identifying step(s) 920.

Disease progression model 140 may train the HMM 930 based on patient progression data corresponding to a plurality of patients having the attribute. For instance, if the patient has a particular attribute (e.g., glaucoma, glaucoma with fast transitions, no history of visual illness, no immediate family history of visual illness, etc.), the HMM may be trained using patient progression data corresponding to patients having the same attribute. In some examples, the HMM may be trained as discussed with respect to FIG. 5. Disease progression model 140 may receive the patient progression data from scrubbed patient database 130.

After training the HMM 930, disease progression model 140 may determine a most probable future disease state 940 using the HMM. For example, at the one or more disease states 330, disease progression model 140 may compute the probabilities of transitioning to the next potential disease state via structural degeneration transition path 340, functional degeneration transition path 350, and structural and functional degeneration transition path 350. Further, disease progression model 140 may calculate the transition probabilities after receiving new or additional patient progression data or other patient data. It is contemplated that disease progression model 140 may determine a most probable future disease state for a most recent disease state (e.g., seventh disease state 470 in FIG. 4) or each disease state along a determined most probable path (e.g., disease states 430, 440, and 450 in FIG. 4) using the HMM.

After determining the most probable future disease state 940, disease progression model 140 may provide the determined most probable future disease state to healthcare provider terminal 110 and/or patient terminal 120 directly or via secure interface 150. The healthcare provider associated with healthcare provider terminal 110 and/or the patient associated with patient terminal 120 may use the determined most probable future disease state to better analyze the progression of the disease for the patient and treat the disease accordingly. By training the HMM based on a patient's attribute(s), disease progression model 140 may more accurately determine the most probable future disease state for the patient.

Figure 10:
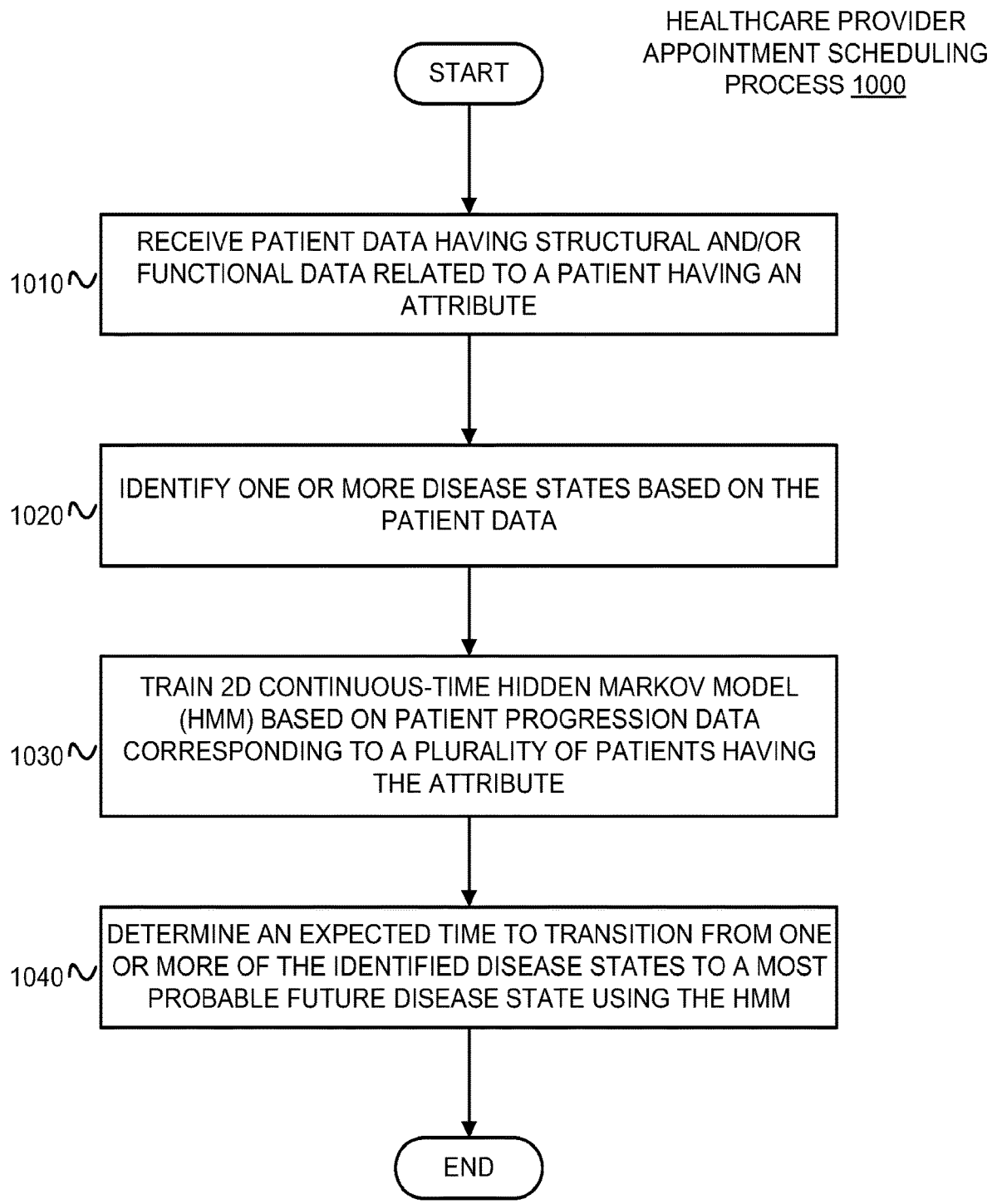
FIG. 10 is a flowchart of an exemplary process for determining when to schedule an appointment with a healthcare provider.

An exemplary process for scheduling a healthcare provider appointment 1000 is shown in FIG. 10. Using the HMM for a patient, disease progression model 140 may predict when the patient's disease may progress to another state or rapidly progress and schedule an appointment with a healthcare provider to monitor the disease progression.

Specifically, in one example, disease progression model 140 may receive patient data 1010 having structural degeneration data 310 and/or functional degeneration data 320 related to a patient having an attribute. It is contemplated, however, that the patient data may not be restricted to a patient having a particular attribute. Disease progression model 140 may receive the patient data directly from healthcare provider terminal 110 and/or patient terminal 120 or indirectly from healthcare provider terminal 110 and/or patient terminal 120 via secure interface 150. The patient data may include structural degeneration data 310 and/or functional degeneration data 320 for an individual patient at two or more points in time.

After receiving patient data 1010, disease progression model 140 may identify or more disease states 1020 based on the patient data. For example, when the structural degeneration data 310 and/or the functional degeneration data 320 in the patient data falls into a range associated with a particular disease state 330, disease progression model 140 may identify that the patient was in that disease state 330 at the time of the visit and/or measurement. Then, disease progression model 140 may identify that the patient was in other disease states 330 at the time of other visits and/or measurements.

In other examples, disease progression model 140 may iteratively receive patient data related to a single point in time and identify a particular disease state 330 associated with the patient at that point in time. As such, it is contemplated that patient data may be received in part or all at once, and may occur before, during, and after identifying step(s) 1020.

Disease progression model 140 may train the HMM 1030 based on patient progression data corresponding to a plurality of patients having the attribute. For instance, if the patient has a particular attribute (e.g., glaucoma, glaucoma with fast transitions, no history of visual illness, no immediate family history of visual illness, etc.), the HMM may be trained using patient progression data corresponding to patients having the same attribute. In some examples, the HMM may be trained as discussed with respect to FIG. 5. Disease progression model 140 may receive the patient progression data from scrubbed patient database 130.

After training the HMM 1030, disease progression model 140 may determine an expected time 1040 to transition from one or more of the identified disease states to a most probable future disease state using the HMM. In some examples, at the one or more disease states 330, disease progression model 140 may compute the probabilities of transitioning to the most probable future disease state via structural degeneration transition path 340, functional degeneration transition path 350, and structural and functional degeneration transition path 360. Further, disease progression model 140 may calculate the transition probabilities after receiving new or additional patient progression data or other patient data. It is contemplated that disease progression model 140 may determine a most probable future disease state for a most recent disease state (e.g., seventh disease state 470 in FIG. 4) or each disease state along a determined most probable path (e.g., disease states 430, 440, and 450 in FIG. 4) using the HMM. Upon determining a most probable future disease state, disease progression model 140 may analyze the patient progression data to determine an expected time to transition to the most probable future disease state.

In other examples, disease progression model 140 may determine an expected time 1040 to transition to a most probable future disease state without determining the most probable future disease state. Disease progression model 140 may compute probabilities of transition to the next potential disease state via structural degeneration transition path 340, functional degeneration transition path 350, and structural and functional degeneration transition path 360, and determine an expected time associated with each transition path 340, 350, and 360. Using the computed probabilities and their corresponding expected times, disease progression model 140 may determine that an expected time 1040 to transition to a most probable future disease state is the sum of each multiplied probability and expected time.

After determining the expected time 1040, disease progression model 140 may provide the determined expected time to healthcare provider terminal 110 and/or patient terminal 120 directly or via secure interface 150. The healthcare provider associated with healthcare provider terminal 110 and/or the patient associated with patient terminal 120 may use the determined expected time to better analyze the progression of the disease for the patient and treat the disease accordingly, which may including scheduling an appointment for the patient with the healthcare provider on, before, or after the expected time. Using this scheduling feature, disease progression model 140 may optimize disease treatment while reducing costs associated with unneeded patient visits to monitor disease progression before a change in the patient's disease state. By training the HMM based on a patient's attribute(s), disease progression model 140 may more accurately determine the most probable future disease state for the patient.

In some examples, future disease state prediction process 900 and/or healthcare provider appointment scheduling process 1000 may be used to predict the occurrence and/or timing of a non-sequential future disease state 330. For example, as shown in FIG. 4, disease progression model 140 may predict a probability that a patient at disease state 420 may end up at disease state 460 in the future. Disease progression model 140 may combine the probability of transition to disease state 460 along each potential transition path between disease state 420 and 460 to determine the total probability of transitioning to disease state 460. Further, disease progression model 140 may determine an expected time associated with the patient transitioning into disease state 460 by determining an expected time and probability for transitioning to each disease state along each potential transition path between disease state 420 and 460. Determining the probability and/or timing of arriving in a future disease state 330 several steps before the transition occurs may allow for improved disease treatment and disease analysis.

Figure 11:
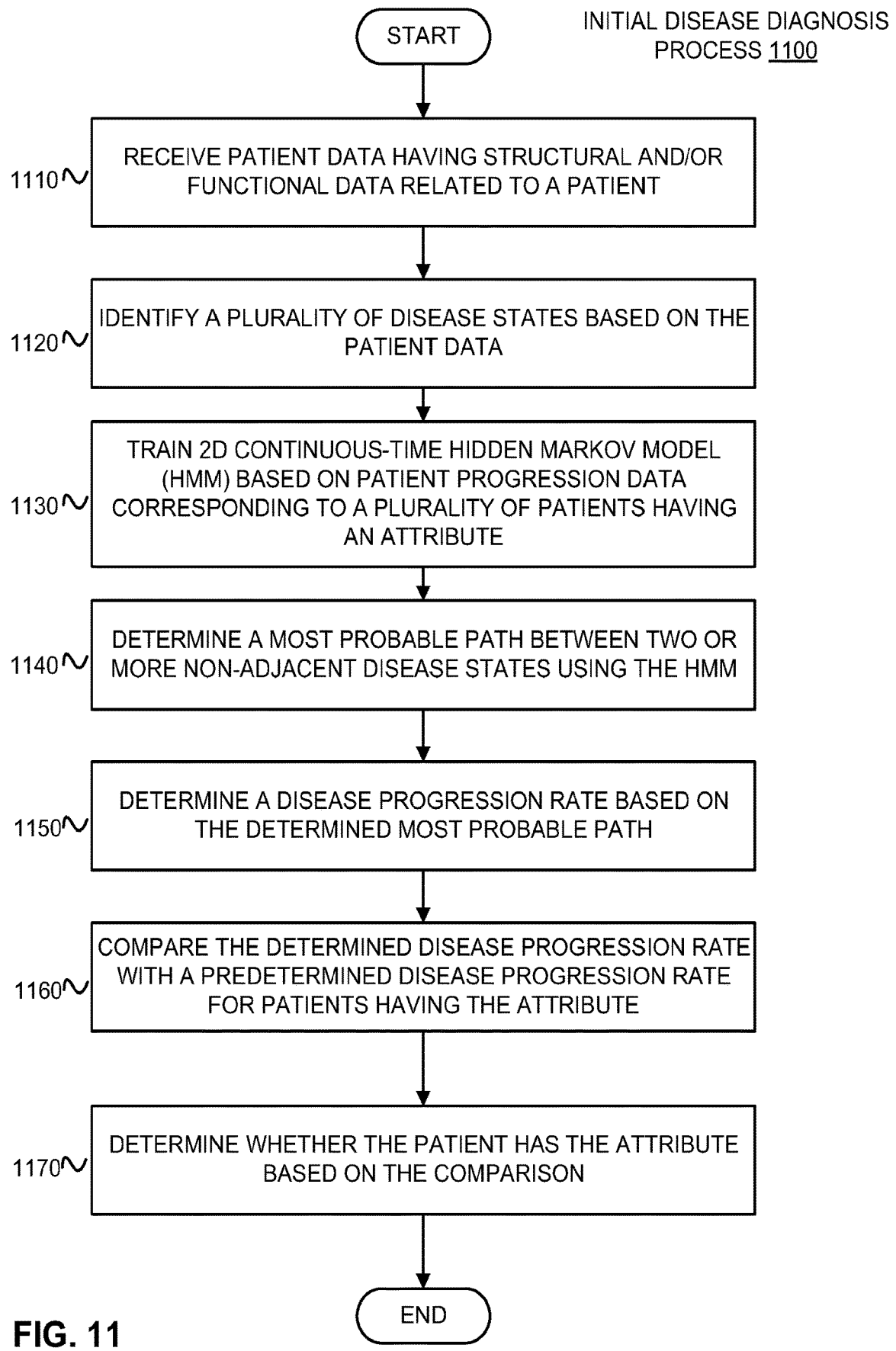
FIG. 11 is a flowchart of an exemplary initial process for diagnosing a disease.

FIG. 11 shows an example of an initial disease diagnosis process 1100. During initial disease diagnosis process 1100, disease progression model 140 may receive patient data 1110 having structural degeneration data 310 and/or functional degeneration data 320 related to a patient. It is contemplated, however, that the patient data may correspond to a patient having a particular attribute. Disease progression model 140 may receive the patient data directly from healthcare provider terminal 110 and/or patient terminal 120 or indirectly from healthcare provider terminal 110 and/or patient terminal 120 via secure interface 150. The patient data may include structural degeneration data 310 and/or functional degeneration data 320 for an individual patient at two or more points in time.

After receiving patient data 1110, disease progression model 140 may identify or more disease states 1120 based on the patient data. For example, when the structural degeneration data 310 and/or the functional degeneration data 320 in the patient data falls into a range associated with a particular disease state 330, disease progression model 140 may identify that the patient was in that disease state 330 at the time of the visit and/or measurement. Then, disease progression model 140 may identify that the patient was in other disease states 330 at the time of other visits and/or measurements.

In other examples, disease progression model 140 may iteratively receive patient data related to a single point in time and identify a particular disease state 330 associated with the patient at that point in time. As such, it is contemplated that patient data may be received in part or all at once, and may occur before, during, and after identifying step(s) 1120.

Disease progression model 140 may train the HMM 1130 based on patient progression data corresponding to a plurality of patients having an attribute. For instance, if the patient has a particular attribute (e.g., glaucoma, glaucoma with fast transitions, no history of visual illness, no immediate family history of visual illness, age-based vision degeneration, etc.), the HMM may be trained using patient progression data corresponding to patients having the same attribute. In some examples, the HMM may be trained as discussed with respect to FIG. 5. Disease progression model 140 may receive the patient progression data from scrubbed patient database 130.

After training the HMM 1130, disease progression model 140 may determine a most probable path 1140 between two or more non-adjacent disease states using the HMM. For example, using the trained parameters, the HMM may use the patient data in its algorithms to determine the most probable path. It is contemplated that, based on the measured or suspected attribute(s) of the patient, the HMM may be trained with patient progression data from a plurality of patients having similar attribute(s), thereby improving accuracy of disease progression model 140.

In determining the most probable path 1140, disease progression model 140 may iteratively update one or more parameters of the HMM until the determined most probable path remains substantially constant. For example, disease progression model 140 may iterate between the E-step and the M-step as it did during training. Further, determining a most probable path 1140 may follow most probable path determination process 700 as described in FIG. 7.

After determining the most probable path 1140, disease progression model 140 may determine a disease progression rate 1150 based on the determined most probable path. For example, the disease progression rate may be the structural and/or functional degeneration of the disease over time.

Once a disease progression rate has been determined 1150, disease progression model 140 may compare 1160 the determined disease progression rate with a predetermined disease progression rate for patients having the attribute corresponding to the patient progression data used to train the HMM 1130. For example, glaucoma patients known to have fast progression may have an average structural and/or functional degeneration rate. Similarly, normal (i.e. non-fast progression) glaucoma patients may have an average structural and/or functional degeneration rate. These average progression rates can be compared, in terms of structural degeneration 310, functional degeneration 320, or both, to the determined disease progression rate of the patient.

Based on the comparison 1160, disease progression model 140 may determine whether the patient has the attribute 1170 based on the comparison. For example, when the patient's disease progression rate does not substantially match the average disease progression rate for a glaucoma patient, disease progression model 140 may determine that the patient does not have glaucoma. Similarly, when the patient's disease progression rate does not substantially match the average disease progression rate for a glaucoma patient having fast progression, disease progression model 140 may determine that the patient does not have fast progression (and the patient may or may not have glaucoma). Depending on the predetermined disease progression rate, substantially matching the progression rate may require a correlation coefficient greater than 0.8.

Disease progression model 140 may provide the determination that a patient does not have an attribute to healthcare provider terminal 110 and/or patient terminal 120 directly or via secure interface 150. The healthcare provider associated with healthcare provider terminal 110 and/or the patient associated with patient terminal 120 may use the determination that a patient does not have an attribute to better analyze the progression of the disease for the patient and treat the disease accordingly.

Figure 12:
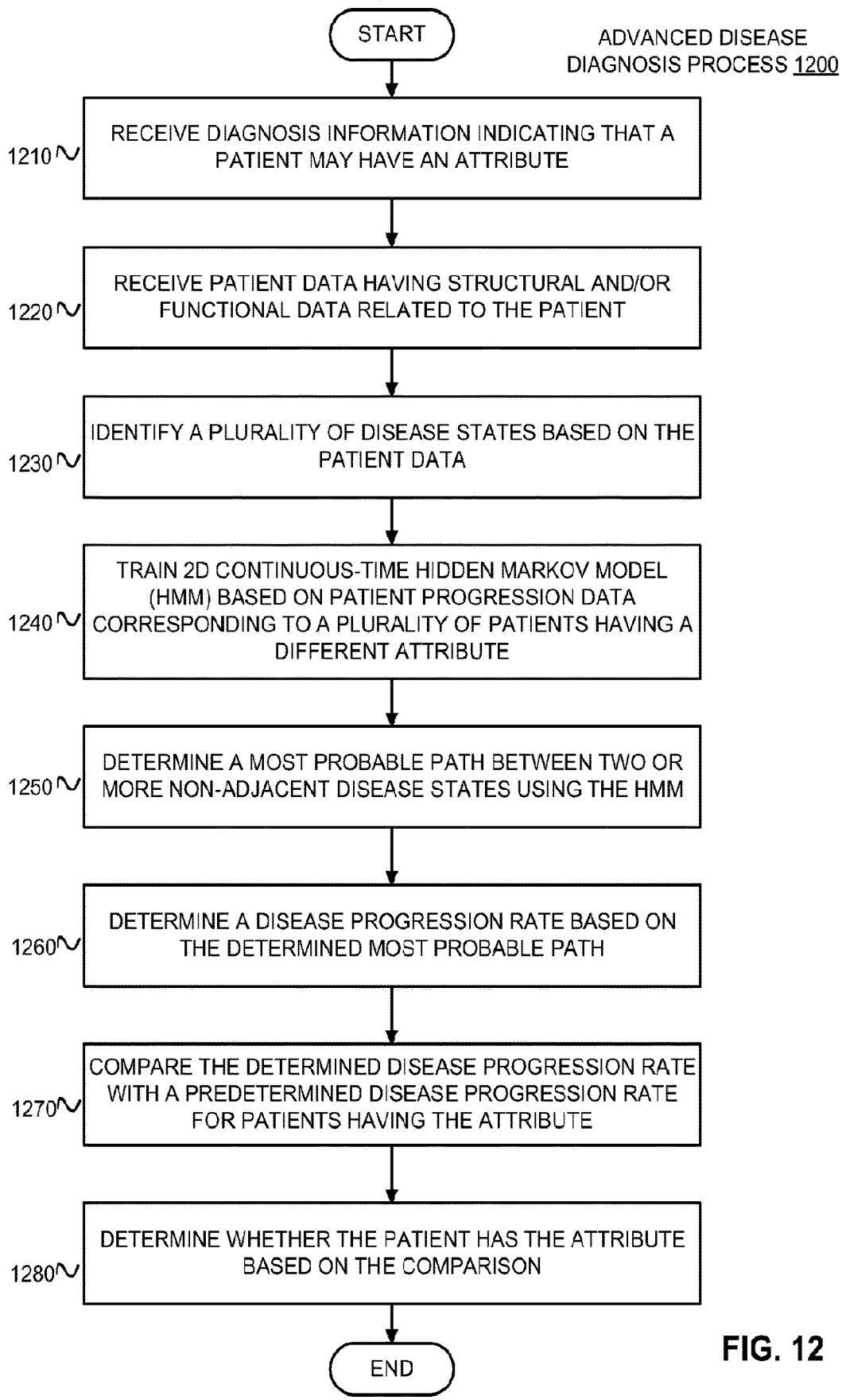
FIG. 12 is a flowchart of an exemplary advanced process for disease diagnosis.

FIG. 12 depicts an example of an advanced disease diagnosis process 1200. During advanced disease diagnosis process 1200, disease progression model 140 may receive diagnosis information indicating that a patient may have an attribute. For example, disease progression model 140 may receive the diagnosis information based on the determination that a patient does not have a different attribute using the initial disease diagnosis process 1100 as shown in FIG. 11. Alternatively, disease progression model 140 may receive the diagnosis information from an outside source, such as healthcare provider terminal 110 and/or patient terminal 120.

After receiving the diagnosis information 1210, disease progression model 140 may receive patient data 1220 having structural degeneration data 310 and/or functional degeneration data 320 related to a patient. It is contemplated, however, that the patient data may correspond to a patient having a particular attribute. Disease progression model 140 may receive the patient data directly from healthcare provider terminal 110 and/or patient terminal 120 or indirectly from healthcare provider terminal 110 and/or patient terminal 120 via secure interface 150. The patient data may include structural degeneration data 310 and/or functional degeneration data 320 for an individual patient at two or more points in time.

After receiving patient data 1220, disease progression model 140 may identify or more disease states 1230 based on the patient data. For example, when the structural degeneration data 310 and/or the functional degeneration data 320 in the patient data falls into a range associated with a particular disease state 330, disease progression model 140 may identify that the patient was in that disease state 330 at the time of the visit and/or measurement. Then, disease progression model 140 may identify that the patient was in other disease states 330 at the time of other visits and/or measurements.

In other examples, disease progression model 140 may iteratively receive patient data related to a single point in time and identify a particular disease state 330 associated with the patient at that point in time. As such, it is contemplated that patient data may be received in part or all at once, and may occur before, during, and after identifying step(s) 1230.

Disease progression model 140 may train the HMM 1240 based on patient progression data corresponding to a plurality of patients having the patient's suspected attribute. For instance, if the patient is suspected of having a particular attribute (e.g., glaucoma, glaucoma with fast transitions, no history of visual illness, no immediate family history of visual illness, age-based vision degeneration, etc.), the HMM may be trained using patient progression data corresponding to patients having the same attribute. In some examples, the HMM may be trained as discussed with respect to FIG. 5. Disease progression model 140 may receive the patient progression data from scrubbed patient database 130.

After training the HMM 1240, disease progression model 140 may determine a most probable path 1250 between two or more non-adjacent disease states using the HMM. For example, using the trained parameters, the HMM may use the patient data in its algorithms to determine the most probable path. It is contemplated that, based on the measured or suspected attribute(s) of the patient, the HMM may be trained with patient progression data from a plurality of patients having similar attribute(s), thereby improving accuracy of disease progression model 140.

In determining the most probable path 1250, disease progression model 140 may iteratively update one or more parameters of the HMM until the determined most probable path remains substantially constant. For example, disease progression model 140 may iterate between the E-step and the M-step as it did during training. Further, determining a most probable path 1250 may follow most probable path determination process 700 as described in FIG. 7.

After determining the most probable path 1250, disease progression model 140 may determine a disease progression rate 1260 based on the determined most probable path. For example, the disease progression rate may be the structural and/or functional degeneration of the disease over time.

Once a disease progression rate has been determined 1260, disease progression model 140 may compare 1270 the determined disease progression rate with a predetermined disease progression rate for patients having the suspected attribute. The predetermined disease progression rate may correspond to the patient progression data used to train the HMM 1240. For example, glaucoma patients known to have fast progression may have an average structural and/or functional degeneration rate. Similarly, normal (i.e. non-fast progression) glaucoma patients may have an average structural and/or functional degeneration rate. These average progression rates can be compared, in terms of structural degeneration 310, functional degeneration 320, or both, to the determined disease progression rate of the patient suspected of having glaucoma with or without fast progression.

Based on the comparison 1270, disease progression model 140 may determine whether the patient has the attribute 1280 based on the comparison. For example, when the patient's disease progression rate substantially matches the average disease progression rate for a glaucoma patient, disease progression model 140 may determine that the patient has glaucoma. Similarly, when the patient's disease progression rate substantially matches the average disease progression rate for a glaucoma patient having fast progression, disease progression model 140 may determine that the patient has glaucoma with fast progression. Depending on the predetermined disease progression rate, substantially matching the progression rate may require a correlation coefficient greater than 0.9.

Disease progression model 140 may provide the determination that a patient has an attribute to healthcare provider terminal 110 and/or patient terminal 120 directly or via secure interface 150. The healthcare provider associated with healthcare provider terminal 110 and/or the patient associated with patient terminal 120 may use the determination that a patient has an attribute to better analyze the progression of the disease for the patient and treat the disease accordingly.

Figure 13:
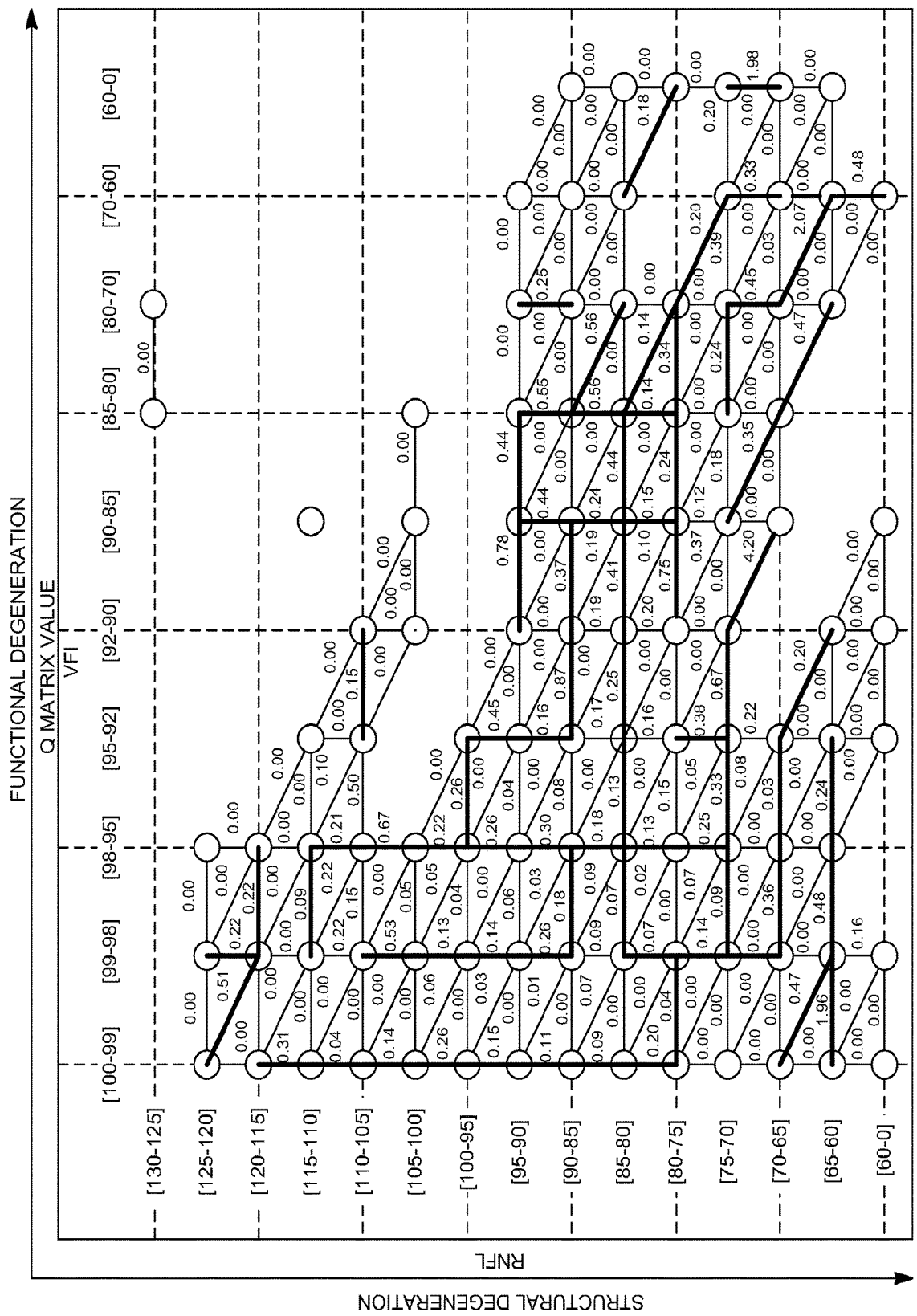
FIG. 13 shows an exemplary chart of the retinal nerve fiber layer versus the visual field index.

FIG. 13 shows an exemplary chart of retinal nerve fiber layer versus visual field index. As shown, there are transition trends for patients based on these structural degeneration data 310 and functional degeneration data 320 measures. Accordingly, disease progression model 140 may determine transition probabilities between disease states 330 based on this data.

Figure 14:
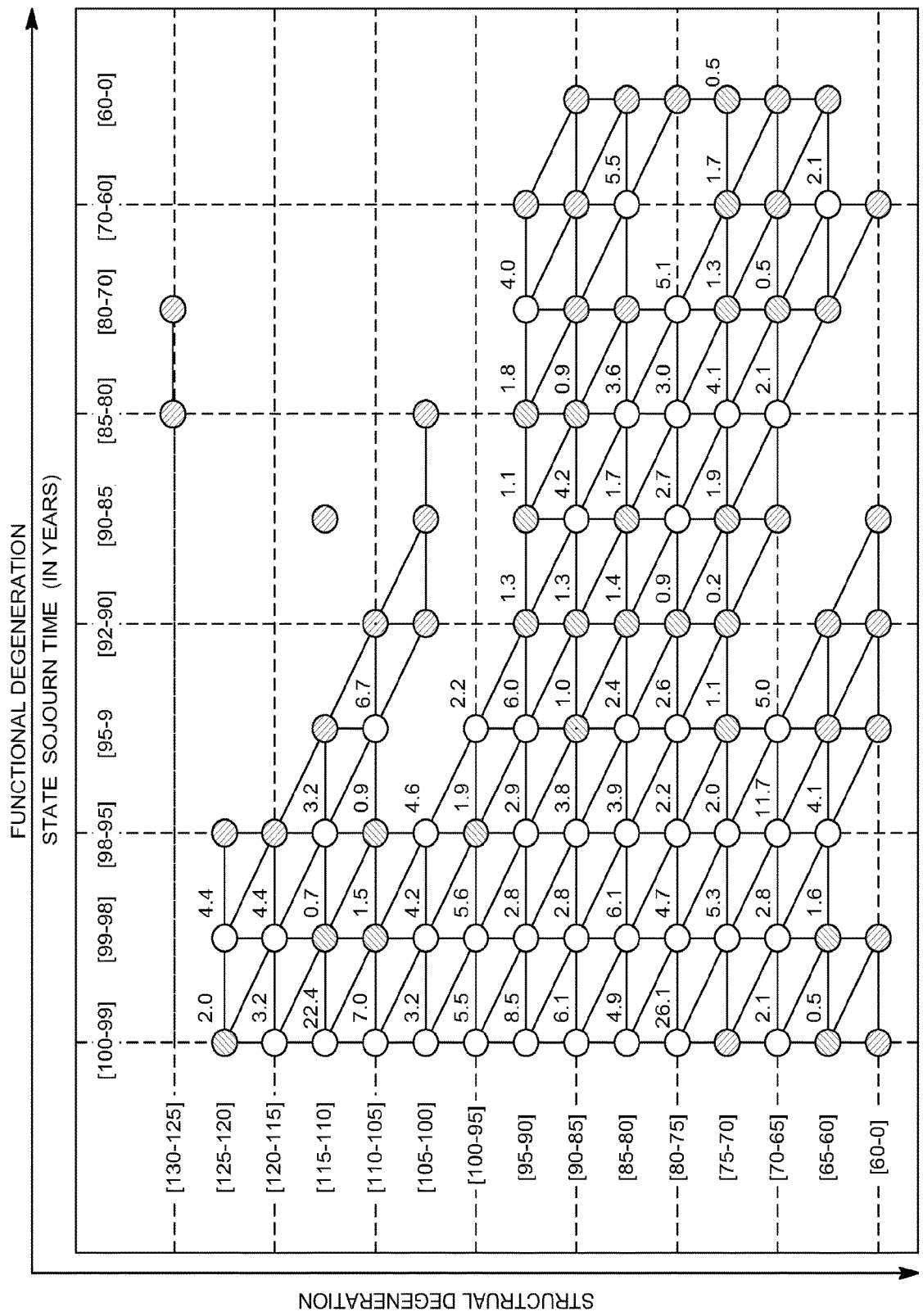
FIG. 14 depicts an exemplary chart showing the relationship between the retinal nerve fiber layer and the disease state sojourn time in years.

FIG. 14 shows an exemplary chart of retinal nerve fiber layer versus disease state sojourn time in years. As shown, certain disease states 330 are frequented more often than others. Accordingly, disease progression model 140 may determine a probability that a patient transitions to one of the disease states 330 based on this data.

Figure 15:
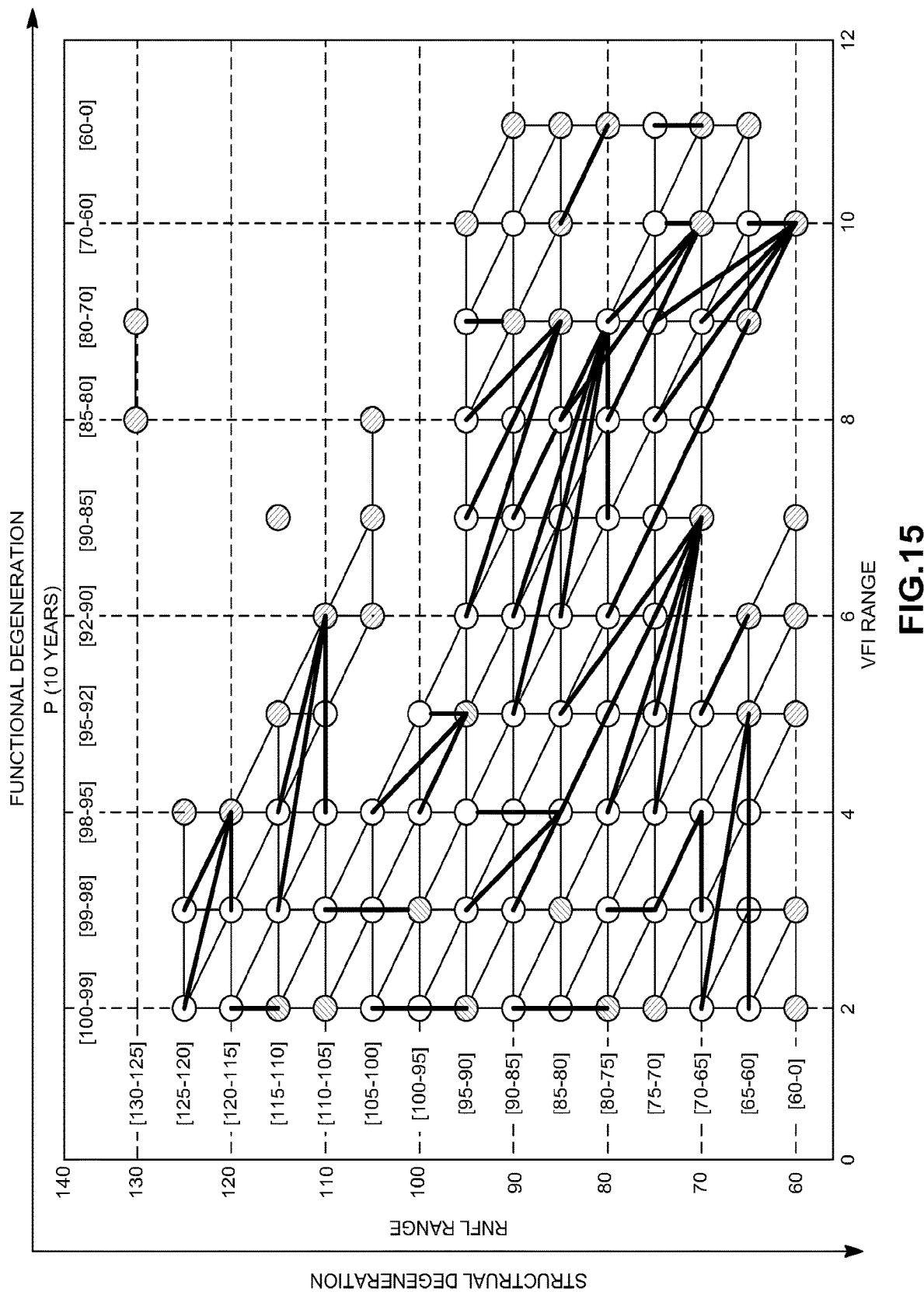
FIG. 15 shows an exemplary chart of the retinal nerve fiber layer versus the disease state sojourn time in years.

FIG. 15 shows an exemplary chart of retinal nerve fiber layer versus disease state sojourn time in years. As shown, certain transition paths between disease states 330 are frequented more often than others. Accordingly, disease progression model 140 may determine transition probabilities between disease states 330 based on this data.

Figure 16:
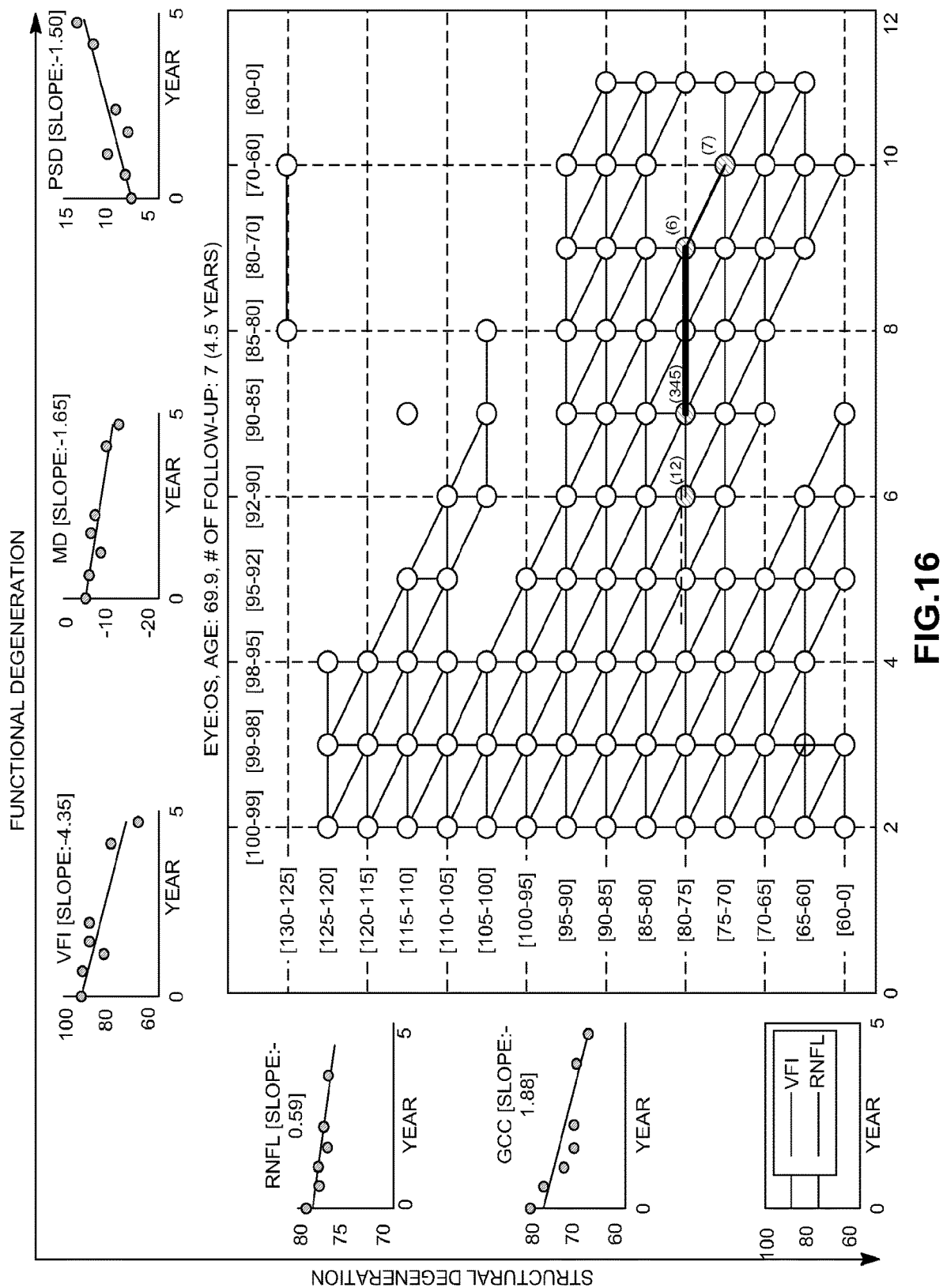
FIG. 16 depicts an exemplary chart showing the relationship between the retinal nerve fiber layer and the disease state sojourn time in years.

FIG. 16 shows an exemplary chart of retinal nerve fiber layer versus disease state sojourn time in years. As shown, a patient's disease progression through a plurality of disease states 330 may be plotted.

In some examples, individualized state transition rates may be modeled using time-varying and/or constant covariate variables (such as age, treatment options, drugs, lab test results, etc.). There are multiple potential advantages to incorporating covariates into the model. First, for example, large numbers of covariates may potentially be added which can describe the impact of additional measurements on the model. This may be useful when two disease states 330 are insufficient to capture all of the factors that influence disease progression. Second, the addition of covariates may not significantly increase the computational burden of model-fitting and the inference of hidden state sequences. For instance, a Cox proportional hazard model may be in the HMM to model the covariate effects with the baseline transition intensity. Using the Cox proportional hazard model to model covariate effects, the new individualized transition intensity becomes:

$$q_{ij,t_k} = q_{ij0} e^{w_1 c_{1,t_k} + w_2 c_{2,t_k} + \ldots + w_n c_{n,t_k}}$$

where $q_{ij0}$ is the baseline transition intensity for the link from state i to j, $(c_{1,t_k}, c_{2,t_k}, \ldots, c_{n,t_k})=C$ are the n covariates of the patient at a particular visit time tk, $(w_1, w_2, \ldots, w_n)=W$ is the weighting for the corresponding covariates, $q_{ij, t_k}$ is the new individualized transition intensity given covariate information at time tk. The parameters W and $q_{ij0}$ may to be estimated from a training dataset. This model represents that one unit of $c_{i,t_k}$ increase is associated with a factor $e^{w_i}$ of baseline transition intensity changes. Note that the incorporation of an additional covariate into the model may only require that a single additional associated weight parameter be added to the set of model parameters. In this manner, many covariates may be employed without substantially increasing the computational cost of model fitting and inference.

It may be assumed that the covariate effect is global or link dependent. When a covariate effect is assumed to be link-dependent, there may be different weighting for differing links for the same covariate variable.

Disease progression model 140 may use a Viterbi-Training based expectation-maximization method to find two sets of parameters W and $q_{ij0}$ alternatively. For example, the Viterbi-training based data likelihood may be:

$$p(O, S^* | \lambda) =$$

$$\max_{S^*=s_1,\ldots,s_n} \left\{ p(o_1|s_1)p(s_1) \prod_{k=2}^{n} p(o_k|s_k)[P_{t_{k-1}}(t_k - t_{k-1})]_{s_{k-1},s_k} \right\}$$

where $\lambda$ is the current model parameters, $O=(o_1, o_2, \ldots, o_n)$ is the observed measurements for the n visits from the subject, $S^*$ is the best state sequence corresponding to the n actual visits, $p(o_k|s_k)$ is the state emission probability, and $$P_{t_{k-1}}(t_k - t_{k-1}) = e^{Q_{t_{k-1}}(t_k - t_{k-1})}$$

is the individualized state transition probability matrix with duration ($t_k-t_{k-1}$), computed from the matrix exponential of transition intensity matrix $Q_{t_{k-1}}$ (using the subject's covariates at time $t_{k-1}$). The $[P(d)]i,j$ entry represents the probability that given the current disease state is si, the disease state will become sj after duration d, with one or more possible intermediary disease states in between.

The overall data likelihood from all patients (K patients) is:

$$\prod_{k=1}^{K} p(O_k, S_k^* | \lambda)$$

In a first step, disease progression model 140 may use the revised HMM that includes covariate effects by first initializing W=0 and $q_{ij0}$ to be a reasonable value for a particular dataset. For example, if a desired average state dwelling time is 2 years, then $$q_i = \sum_{j,j \neq i} q_{ij} = 1/(\text{average state dwelling time}) = 1/2 = 0.5.$$

Disease progression model 140 may then set all intermediary disease states along from state i to have equal rate, such that their sum is 0.5.

After initializing the revised HMM, disease progression model 140 may update $q_{ij0}$ parameters in a second step. For example, disease progression model 140 may use current model parameters to determine a most probable path and a disease state duration for each patient. Disease progression model 140 may then compute a new average disease state transition rate for each link as follows:

$$q_{ij,ave} = \frac{N_{ij}}{T_i} \approx \frac{q_{ij0}\left[e^{WC_{P1}+WC_{P2}+\ldots+WC_{PN_i}}\right]}{N_i}$$

where $N_{ij}$ is the number of patients passing the most probable path between disease states $s_i$ and $s_j$, $T_i$ is the total duration from patients passing state $s_i$, $N_i$ is the number of patients passing state $s_i$, $(P_1, P_2, \ldots P_{Ni})$ represent the subjects that pass state $s_1$. The last term represents that $q_{ij,ave}$ may be computed as the average individualized state transition rates along link i,j for all patients that pass state $s_1$. $C_{pi}$ may be the covariate vector of patient $p_i$ when the patient passes state $s_i$.

Disease progression model 140 may then derive the update rule for $q_{ij0}$ by rearranging the terms:

$$q_{ij0} = \frac{N_{ij}N_i}{T_i\left[e^{WC_{P1}+WC_{P1}+\ldots+WC_{PN_i}}\right]}$$

In a third step, disease progression model 140 may optimize W parameters by fixing $q_{ij0}$ parameters to current values and by directly maximizing the overall data likelihood using a standard numerical optimization algorithm, such as Broyden-Fletcher-Goldfarb-Shanno algorithm.

$$\max_W \prod_{k=1}^{K} p(O_k, S_k^* | \lambda)$$

In a fourth step, disease progression model 140 may iterate steps 2 and 3 until the overall data likelihood reaches a substantially fixed point.

While the present disclosure has been described in connection with a plurality of exemplary aspects, as illustrated in the various figures and discussed above, it is understood that other similar aspects can be used or modifications and additions can be made to the described aspects for performing the same function of the present disclosure without deviating therefrom. For example, in various aspects of the disclosure, methods and compositions were described according to aspects of the presently disclosed subject matter. However, other equivalent methods or composition to these described aspects are also contemplated by the teachings herein. Therefore, the present disclosure should not be limited to any single aspect, but rather construed in breadth and scope in accordance with the appended claims.

The invention claimed is:

1. A method for determining a disease state transition path of glaucoma, said method comprising:
   receiving, by a first processor of a disease progression model, patient data comprising structural degeneration data and functional degeneration data related to a patient, via a secure interface, from a second processor associated with a healthcare provider terminal;
   identifying, by the first processor, based on the patient data, a first disease state of a plurality of non-overlapping disease states of glaucoma each associated with a predetermined range of one or both of functional and structural degeneration values;
   identifying, by the first processor, based on the patient data, a second disease state of the plurality of disease states, wherein the second disease state is non-adjacent to the first disease state;

predicting, by the first processor using a two dimensional continuous-time hidden Markov model, a most probable path between the first disease state and the second disease state, wherein the most probable path comprises one or more intermediary disease states of the plurality of disease states, wherein each intermediary disease state is adjacent to one or more of the first disease state, the second disease state, and another intermediary disease state;

outputting, by the first processor, the most probable path between the first disease state and the second disease state to cause the healthcare provider terminal to display the most probable path as a graphical user interface;

training, by the first processor, the hidden Markov model based on patient progression data corresponding to a plurality of patients having an attribute;

predicting, with the first processor using a trained hidden Markov model, an updated most probable path between the first disease state and the second disease state;

predicting, with the first processor, a disease progression rate based on the updated most probable path;

comparing, by the first processor, the predicted disease progression rate with a predetermined disease progression rate; and predicting, with the first processor, whether a patient has the attribute based on the comparison.

2. The method of claim 1, wherein each sequential disease state is associated with one or both of increased structural and functional degeneration values as time progresses.

3. The method of claim 1 further comprising iteratively updating, by the first processor, one or more parameters of the hidden Markov model based on the determined most probable path until the most probable path remains substantially constant.

4. The method of claim 1, wherein predicting the most probable path further comprises:
   predicting the most probable path, with the first processor using hidden Markov model and assigning, by the first processor, a uniform time spent in each intermediary state along the most probable path;
   updating, by the first processor, one or more parameters of the hidden Markov model based on the determined most probable path;
   predicting, by the first processor, the most probable path using the hidden Markov model; and
   alternating, by the first processor, the updating and redetermining steps until the redetermined most probable path substantially matches a previously determined most probable path.

5. The method of claim 1 further comprising predicting, with the first processor, a most probable next disease state for one or more disease states along the most probable path or for the second disease state using the hidden Markov model.

6. The method of claim 5 further comprising:
   comparing, by the first processor, the most probable next disease state with the second disease state; and
   predicting, with the first processor, that a transition between disease states along the most probable path has a fast structural and/or functional progression based on the comparison.

7. The method of claim 5 further comprising predicting, with the first processor, an expected time to transition from the second disease state to the most probable next disease state using the hidden Markov model.

8. A method for detecting disease state transitions of glaucoma, said method comprising:
   receiving, by a first processor of a disease progression model, patient data comprising structural degeneration data and functional degeneration data related to a patient, via a secure interface, from a second processor associated with a healthcare provider terminal;
   identifying, by the first processor, based on the patient data, a first disease state of a plurality of non-overlapping disease states of glaucoma each associated with a predetermined range of one or both of functional and structural degeneration values;
   identifying, by the first processor, based on the patient data, a second disease state of the plurality of disease states, wherein the second disease state is non-adjacent to the first disease state;
   determining, with the first processor using a two dimensional continuous-time hidden Markov model, a most probable path between the first disease state and the second disease state, wherein:
      the most probable path comprises one or more intermediary disease states of the plurality of disease states, and
      each intermediary disease state is adjacent to one or more of the first disease state, the second disease state, and another intermediary disease state;
   determining, with the first processor, a most probable next disease state for one or more disease states along the most probable path using the hidden Markov model;
   comparing, by the first processor, the most probable next disease state with the second disease state;
   determining, with the first processor, that a transition between disease states along the most probable path has a fast structural and/or functional progression based on the comparison;
   when the transition is determined to be the fast structural and/or functional progression, training, by the first processor, the hidden Markov model based on patient progression data corresponding to a plurality of patients having the fast structural and/or functional progression; and
   redetermining, with the first processor, the most probable next disease state for one or more disease states along the most probable path using the hidden Markov model.

9. The method of claim 8, wherein each sequential disease state is associated with one or both of increased functional and structural degeneration values as time progresses.

10. The method of claim 8 further comprising iteratively updating, by the first processor, one or more parameters of the hidden Markov model based on the determined most probable path until the most probable path remains substantially constant.

11. A system for determining a disease state transition path of glaucoma, said method comprising:
   a storage device for storing instructions; and
   a processor configured to execute the instructions in the storage device to:
      receive patient data comprising structural degeneration data and functional degeneration data related to a patient;
      identify, based on the patient data, two or more disease states of a plurality of nonoverlapping disease states of glaucoma each associated with a predetermined range of one or both of functional and structural degeneration values;

predict, using a two dimensional continuous-time hidden Markov model, a most probable path between a sequential pair of non-adjacent disease states of the two or more disease states, wherein the most probable path comprises one or more intermediary disease states of the plurality of disease states,
  wherein each intermediary disease state is adjacent to at least one of the sequential pair of non-adjacent disease states and another intermediary disease state;
train the hidden Markov model based on patient progression data corresponding to a plurality of patients having an attribute;
predict, using a trained hidden Markov model, an updated most probable path between the sequential pair of non-adjacent disease states;
predict a disease progression rate based on the updated most probable path;
  compare the predicted disease progression rate with a predetermined disease progression rate; and
  determine whether a patient has the attribute based on the comparison.

12. The system of claim 11, wherein each of the identified two or more disease states is associated with one or both of increased functional and structural degeneration values as time progresses.

13. The system of claim 11, wherein the processor is further configured to predict a most probable future disease state for the most recent of the identified two or more disease states using the hidden Markov model.

14. The system of claim 13, wherein the processor is further configured to predict an expected time to transition from the most recent of the identified two or more disease state to the most probable future disease state using the hidden Markov model.

* * * * *